US011406340B2

United States Patent
Kondo et al.

(10) Patent No.: US 11,406,340 B2
(45) Date of Patent: Aug. 9, 2022

(54) METHOD FOR CONVERTING TONE OF CHEST X-RAY IMAGE, STORAGE MEDIUM, IMAGE TONE CONVERSION APPARATUS, SERVER APPARATUS, AND CONVERSION METHOD

(71) Applicant: Panasonic Corporation, Osaka (JP)

(72) Inventors: Kenji Kondo, Ibaraki (JP); Jun Ozawa, Nara (JP); Hirohiko Kimura, Fukui (JP); Harumi Itoh, Fukui (JP); Shinichi Fujimoto, Fukui (JP)

(73) Assignee: Panasonic Corporation, Osaka (JP)

( * ) Notice: Subject to any disclaimer, the term of this patent is extended or adjusted under 35 U.S.C. 154(b) by 94 days.

(21) Appl. No.: 17/088,657

(22) Filed: Nov. 4, 2020

(65) Prior Publication Data

US 2021/0045704 A1 Feb. 18, 2021

Related U.S. Application Data

(63) Continuation of application No. PCT/JP2019/015880, filed on Apr. 12, 2019.

(30) Foreign Application Priority Data

May 16, 2018 (JP) .............................. JP2018-094737

(51) Int. Cl.
*A61B 5/11* (2006.01)
*A61B 6/00* (2006.01)
*G06N 20/00* (2019.01)

(52) U.S. Cl.
CPC ............ *A61B 6/5205* (2013.01); *A61B 6/461* (2013.01); *A61B 6/484* (2013.01); *A61B 6/50* (2013.01); *G06N 20/00* (2019.01)

(58) Field of Classification Search
CPC ..... A61B 5/1128; A61B 5/113; A61B 6/5217; A61B 6/50; A61B 6/5205; A61B 6/484;
(Continued)

(56) References Cited

U.S. PATENT DOCUMENTS

2018/0108156 A1   4/2018 Kobayashi

FOREIGN PATENT DOCUMENTS

JP      2005005845 A  *  1/2005
JP      2010-259540       11/2010
(Continued)

OTHER PUBLICATIONS

International Search Report of PCT application No. PCT/JP2019/015880 dated Jul. 2, 2019.
(Continued)

*Primary Examiner* — Don K Wong
(74) *Attorney, Agent, or Firm* — Wenderoth, Lind & Ponack, L.L.P.

(57) ABSTRACT

A method for converting tone of a chest X-ray image includes obtaining a target chest X-ray image, detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line, extracting a pixel group corresponding to a neighboring area of the structure, generating a contrast conversion expression for histogram equalization using a histogram of the pixel group, and converting luminance of each pixel value in entirety of the target chest X-ray image using the contrast conversion expression.

14 Claims, 21 Drawing Sheets

(58) Field of Classification Search
CPC ....... A61B 6/52; A61B 6/5258; A61B 6/5211; G06N 20/00; G06T 5/50; G06T 2207/10072; G06T 2207/10116; G06T 2207/20172; G06T 5/00
See application file for complete search history.

(56) References Cited

FOREIGN PATENT DOCUMENTS

| | | |
|---|---|---|
| JP | 2012-228407 | 11/2012 |
| JP | 2017-018339 | 1/2017 |
| JP | 2018-000312 | 1/2018 |
| JP | 2018-064627 | 4/2018 |
| WO | 2015/174206 | 11/2015 |
| WO | WO-2019220825 A1 * 11/2019 ............. A61B 6/461 |

OTHER PUBLICATIONS

Olaf Ronneberger et al., "U-Net: Convolutional Networks for Biomedical Image Segmentation", Medical Image Computing and Computer-Assisted Intervention (MICCAI), Springer, LNCS, vol. 9351, pp. 234-241, Nov. 18, 2015.

Jonathan Long et al., "Fully Convolutional Networks for Semantic Segmentation", In CVPR, Nov. 14, 2014.

Takashi Ishidate, "Correction of Color Image by Histogram Stretching and Equalization", CodeZine, Web Magazine about Implementation for Developers, Dec. 7, 2005, <URL:https://codezine.jp/article/detail/214>.

Xiaosong Wang et al., "ChestX-ray8: Hospital-scale Chest X-ray Database and Benchmarks on Weakly-Supervised Classification and Localization of Common Thorax Diseases", CVPR, May 5, 2017.

* cited by examiner

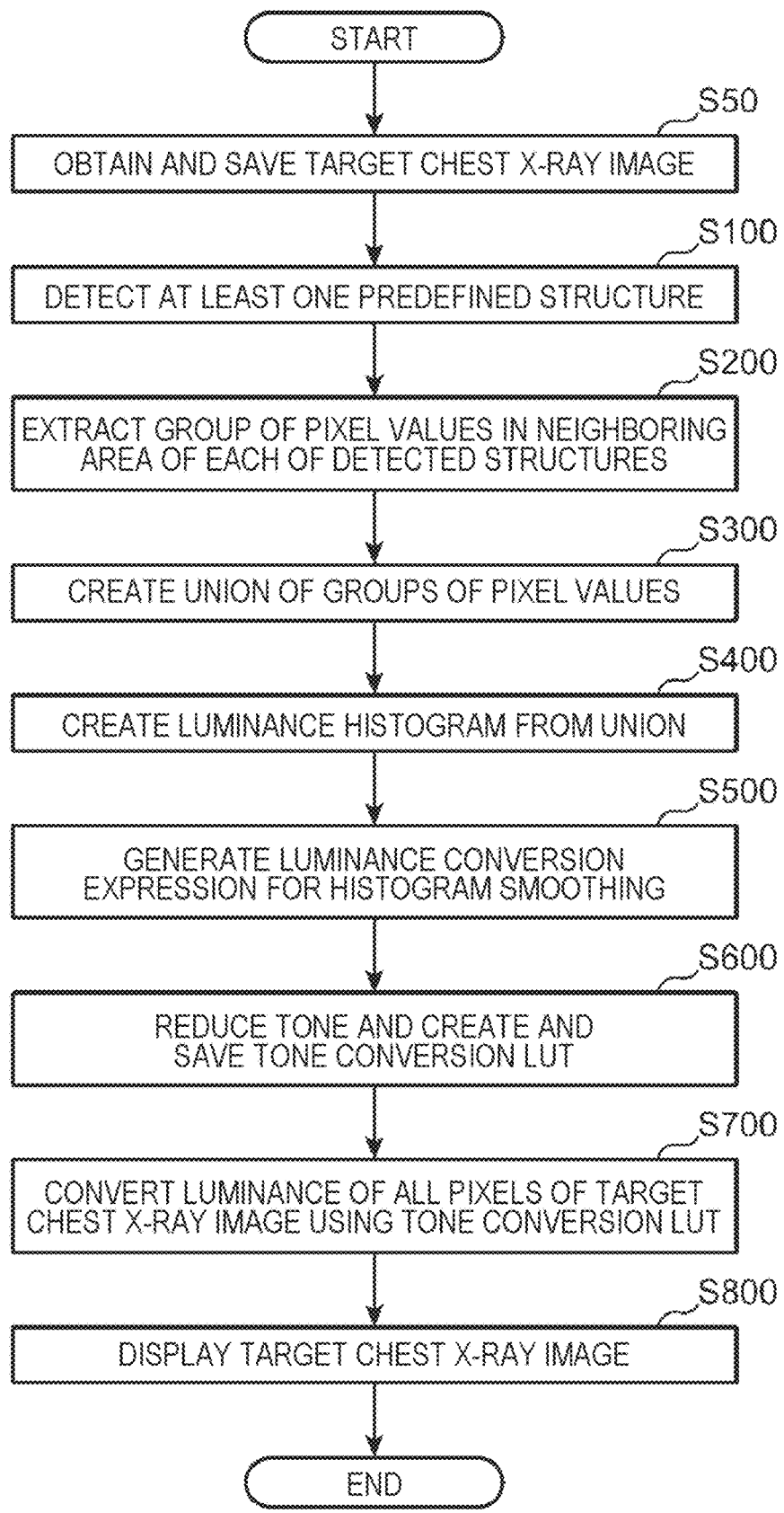

Ix

Px

Ix

Pz

FIG. 9A
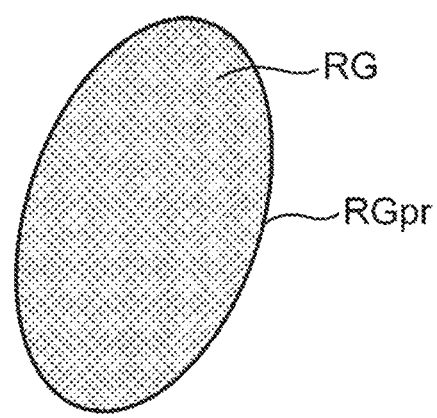
FIG. 9B
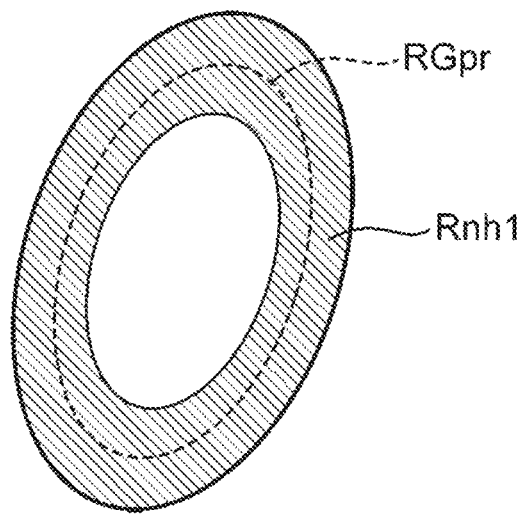
FIG. 10
1000
| z | 0 | ... | z | ... | 4095 |
|---|---|-----|---|-----|------|
| t(z) | 0 | ... | q(z)/16 | ... | 255 |

| STRUCTURE ID (ID=0, 1, ..., N−1) | RESOLUTION i (i=0, 1, 2, OR 3) |
|---|---|
| STRUCTURE 0 | 0 |
| STRUCTURE 1 | 2 |
| ... | ... |
| STRUCTURE (N−1) | 1 |

METHOD FOR CONVERTING TONE OF CHEST X-RAY IMAGE, STORAGE MEDIUM, IMAGE TONE CONVERSION APPARATUS, SERVER APPARATUS, AND CONVERSION METHOD

BACKGROUND

1. Technical Field

The present disclosure relates to a technique for processing medical images and, more specifically, to a technique for converting tone of a chest X-ray image.

2. Description of the Related Art

Costs of devices for capturing chest X-ray images and costs of capturing chest X-ray images are especially low among medical images, and such devices are widely used. Chest X-ray images, therefore, are a first choice for making diagnoses of chest diseases. In chest X-ray images, however, anatomical structures overlap one another in a depth direction. For this reason, interpretation is difficult, and there are problems that lesions can be overlooked and that computer tomography is performed without much consideration.

An X-ray image capture apparatus usually obtains a chest X-ray image as a fine-gradation (e.g., 10 to 14 bits) digital image. When the obtained chest X-ray image is displayed on a monitor, however, the chest X-ray image is subjected to tone compression to achieve coarser gradation (e.g., 8 to 12 bits) and displayed. The tone compression is performed along with contrast conversion such as gamma correction so that important tones in the image are saved. In order to make interpretation as easy as possible, it is important to perform tone compression such that information in an area important in making a diagnosis based on the chest X-ray image does not deteriorate.

International Publication No. 2015/174206 has proposed a technique for converting tone capable of displaying a desired area with desired levels of contrast and density while maintaining the amount of information of a chest X-ray image. In the technique described in International Publication No. 2015/174206, a range of pixel values in a broad area such as a lung field or a mediastinum is estimated from a pixel value histogram of a chest X-ray image, and a control point of a gamma curve is determined on the basis of a result of the estimation.

SUMMARY

In the technique described in International Publication No. 2015/174206, for example, a gamma curve suitable for a lung field or a mediastinum, for example, can be used. Because the example of the related art does not necessarily improve a level of contrast in an area important in making a diagnosis based on a chest X-ray image, however, further improvements are required.

In one general aspect, the techniques disclosed here feature a method for converting tone of a chest X-ray image, the method being performed by a computer of an image tone conversion apparatus that converts tone of a target chest X-ray image, which is a chest X-ray image to be interpreted, the method including obtaining the target chest X-ray image, detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line, extracting a pixel group corresponding to a neighboring area of the structure, generating a contrast conversion expression for histogram equalization using a histogram of the pixel group, and converting luminance of each pixel value in entirety of the target chest X-ray image using the contrast conversion expression.

The above aspect achieves further improvements.

It should be noted that this general or specific aspect may be implemented as an apparatus, a system, an integrated circuit, a computer program, a computer-readable storage medium, or any selective combination thereof. The computer-readable storage medium may be a nonvolatile storage medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a flowchart according to the first embodiment;

FIG. 9A is a diagram schematically illustrating an example of an area structure;

FIG. 9B is a diagram schematically illustrating an example of a neighboring area of the area structure illustrated in FIG. 9A;

FIG. 10 is a diagram schematically illustrating an example of a tone conversion lookup table (LUT);

FIG. 14 is a diagram schematically illustrating resolution information;

DETAILED DESCRIPTION

Figure 1:
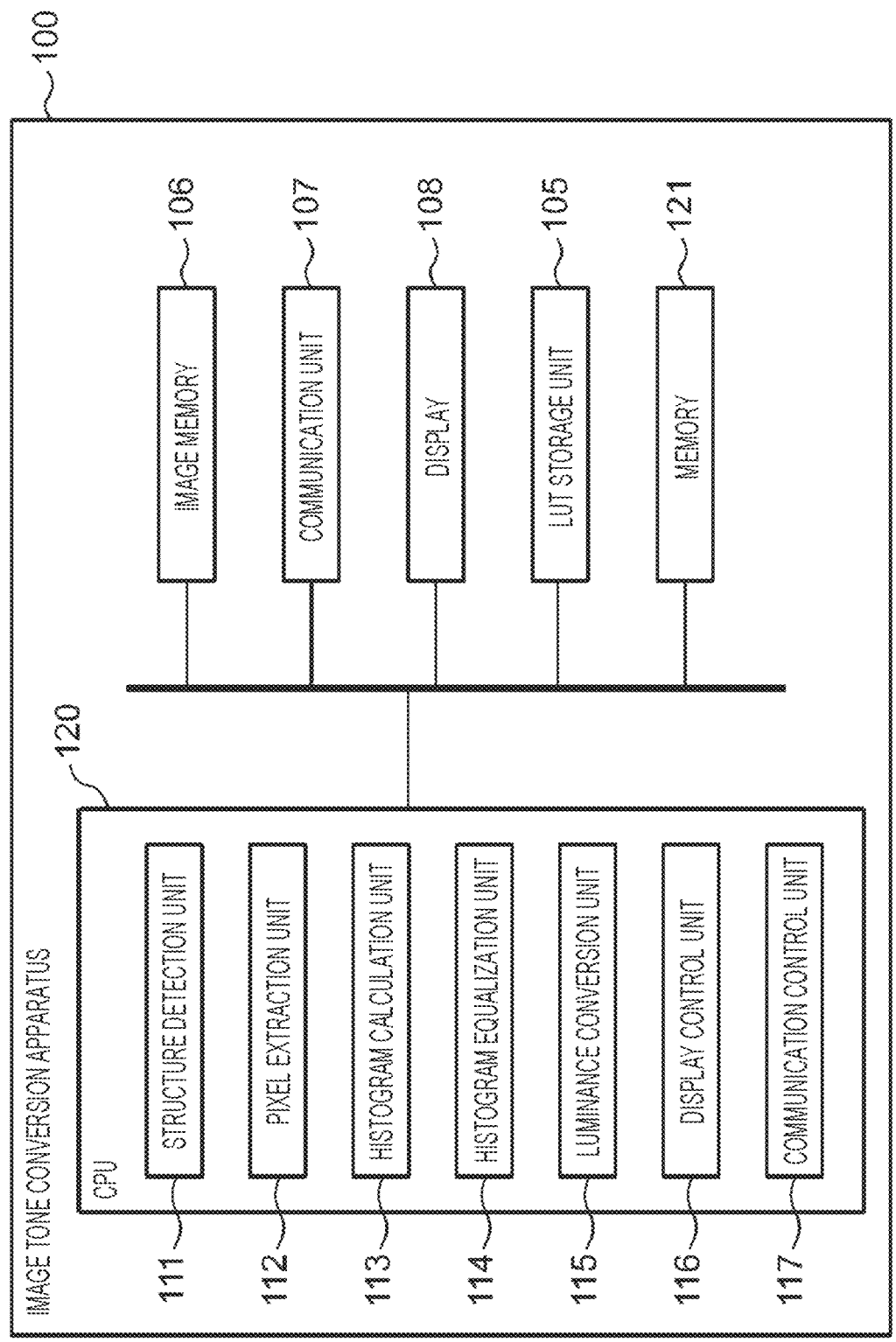
FIG. 1 is a block diagram illustrating an image tone conversion apparatus according to a first embodiment.

Underlying Knowledge Forming Basis of Present Disclosure

With the technique described in International Publication No. 2015/174206, a gamma curve suitable for a lung field or a mediastinum, for example, can be used. The present inventor, however, has found that an area in a chest X-ray image that is smaller than a lung field or a mediastinum and whose range of shades is smaller than that of the lung field or the mediastinum can be sometimes important in making a diagnosis. The technique described in International Publication No. 2015/174206 does not necessarily improve a level of contrast in such an area.

The present inventor has arrived at the following aspects, in which a level of contrast in a small area in a chest X-ray image whose range of shades is small (e.g., a linear structure that will be described later) and that is important in making a diagnosis based on the chest X-ray image can be improved.

A first aspect of the present disclosure is
a method for converting tone of a chest X-ray image, the method being performed by a computer of an image tone conversion apparatus that converts tone of a target chest X-ray image, which is a chest X-ray image to be interpreted, the method including:
obtaining the target chest X-ray image;
detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;
extracting a pixel group corresponding to a neighboring area of the structure;
generating a contrast conversion expression for histogram equalization using a histogram of the pixel group; and
converting luminance of each pixel value in entirety of the target chest X-ray image using the contrast conversion expression.

A second aspect of the present disclosure is
a storage medium storing a program for causing a computer of an image tone conversion apparatus that converts tone of a target chest X-ray image, which is a chest X-ray image to be interpreted, to perform a process, the storage medium being nonvolatile and computer-readable, the process including:
obtaining the target chest X-ray image;
detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;
extracting a pixel group corresponding to a neighboring area of the structure;
generating a contrast conversion expression for histogram equalization using a histogram of the pixel group; and
converting luminance of each pixel value in entirety of the target chest X-ray image using the contrast conversion expression.

A third aspect of the present disclosure is
an image tone conversion apparatus including:
an obtainer that obtains a target chest X-ray image, which is a chest X-ray image to be interpreted;
a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;
an extractor that extracts a pixel group corresponding to a neighboring area of the structure;
an equalizer that generates a contrast conversion expression for histogram equalization using a histogram of the pixel group; and
a luminance converter that converts luminance of each pixel value in entirety of the target chest X-ray image using the contrast conversion expression.

In the first to third aspects, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line is detected in a target chest X-ray image, which is a chest X-ray image to be interpreted, using a model obtained as a result of machine learning. A pixel group corresponding to a neighboring area of the detected structure is extracted. A contrast conversion expression for histogram equalization is generated using a histogram of the extracted pixel group. Luminance of each pixel value in the entirety of the target chest X-ray image is converted using the generated contrast conversion expression. According to the first to third aspects, therefore, a level of contrast in a neighboring area of a structure can be improved without being affected by pixels having pixel values whose frequencies are high.

In the first aspect, for example,
the model obtained as a result of the machine learning may be a model subjected to the machine learning such that the structure is detected in a learning chest X-ray image, which is a chest X-ray image in a normal state, using a neural network that performs prediction in units of pixels.

In this aspect, a structure is detected using a model subjected to machine learning such that a structure is detected in a learning chest X-ray image, which is a chest X-ray image in a normal state, using a neural network that performs prediction in units of pixels, Since the prediction is performed in units of pixels, a structure including a linear structure formed of a first linear area or a second linear area can be accurately detected.

In the first aspect, for example,
in the detecting, a first X-ray image may be created by converting a resolution of the target chest X-ray image into a first resolution, which is lower than the resolution of the target chest X-ray image,
a second X-ray image may be created by converting the resolution of the target chest X-ray image into a second resolution, which is higher than the first resolution but equal to or lower than the resolution of the target chest X-ray image,
a structure of a first size may be detected from the first X-ray image,
a search area smaller than the second X-ray image may be set in the second X-ray image on a basis of a result of the detection of the structure of the first size, and
a structure of a second size, which is smaller than the first size, may be detected in the search area.

In this aspect, a structure of a first size is detected from a first X-ray image of a first resolution. A search area is set in a second X-ray image of a second resolution, which is higher than the first resolution, and a structure of a second size, which is smaller than the first size, is detected in the search area. According to this aspect, therefore, a search area smaller than the target chest X-ray image is set when a high-resolution image is used. As a result, the amount of memory used is reduced. Consequently, even when memory capacity is low, a decrease in structure detection performance can be suppressed.

In the first aspect, for example,
in the detection of the structure of the first size, an anatomical structure may be detected from the first X-ray image as the structure of the first size, and
in the detection of the structure of the second size, a linear structure may be detected in the search area of the second X-ray image as the structure of the second size.

According to this aspect, since the anatomical structure is of the first size, which is relatively large, the anatomical structure can be appropriately detected from the first X-ray image of the first resolution, which is relatively low. In addition, since the linear structure is of the second size, which is relatively small, the linear structure can be appropriately detected in the search area set in the second X-ray image of the second resolution, which is relatively high.

In the first aspect, for example,
in the setting of the search area, the search area may be set using a relative positional relationship between the structure of the first size and the structure of the second size read from a position memory storing the relative positional relationship in advance.

According to this aspect, a position of a structure of the second size can be detected from a position of a structure of the first size obtained as a result of a first detection sub-step and a relative positional relationship between the structure of the first size and the structure of the second size. The structure of the second size, therefore, can be certainly detected by setting a search area such that the search area includes the detected position of the structure of the second size.

In the first aspect, for example,
in the extracting, an area obtained by expanding a contour of the structure outward and inward by a certain number of pixels may be determined as the neighboring area of the structure.

In this aspect, a pixel group in an area extending outside a contour of a structure over a certain number of pixels and a pixel group in an area extending inside the contour of the structure over the certain number of pixels are extracted. According to this aspect, therefore, a level of contrast of the contour of the structure can be improved. As a result, the structures becomes easier to visually recognize.

In the first aspect, for example,
in the extracting, an area obtained by expanding the structure outward by a certain number of pixels may be determined as the neighboring area of the structure.

In this aspect, a pixel group in an area obtained by expanding a structure outward by a certain number of pixels is extracted. According to this aspect, therefore, a level of contrast in an area larger than a structure by the certain number of pixels can be improved. As a result, the structure becomes easier to visually recognize.

In the first aspect, for example,
in the extracting, all detected structures may be used.

According to this aspect, levels of contrast in all neighboring areas of detected structures can be improved.

The first aspect may further include, for example,
selecting, by a user, at least one of detected structures.

In the extracting, only the at least one of the detected structures selected by the user may be used.

According to this aspect, a level of contrast in a neighboring area of a desired structure can be improved by selecting the desired structure.

The first aspect may further include, for example,
displaying, on a display, the target chest X-ray image whose luminance has been converted.

In the converting of the luminance, the luminance of each pixel value in the entirety of the target chest X-ray image may be converted using the contrast conversion expression and a tone reduction expression for reducing the tone of the target chest X-ray image.

According to this aspect, even when tone that can be displayed on a display is lower than that of a target chest X-ray image, the target chest X-ray image whose level of contrast in a neighboring area of a structure has been improved can be displayed on the display with tone suitable for the display.

A fourth aspect of the present disclosure is
a server apparatus including:
an obtainer that obtains a target chest X-ray image, which is a chest X-ray image to be interpreted;
a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;
an extractor that extracts a pixel group corresponding to a neighboring area of the structure; and
an equalizer that generates a contrast conversion expression for histogram equalization using a histogram of the pixel group; and a luminance converter that converts luminance of each pixel value in entirety of the target chest X-ray image using the contrast conversion expression; and a communication controller that transmits the target chest X-ray image whose luminance has been converted to an external terminal apparatus.

In the fourth aspect, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line is detected in a target chest X-ray image, which is a chest X-ray image to be interpreted, using a model obtained as a result of machine learning. A pixel group corresponding to a neighboring area of the detected structure is extracted. A contrast conversion expression for histogram equalization is generated using a histogram of the extracted pixel group. Luminance of each pixel value in the entirety of the target chest X-ray image is converted using the generated contrast conversion expression. The target chest X-ray image whose luminance has been converted is transmitted to an external terminal apparatus. According to the fourth aspect, therefore, a user of a terminal apparatus can obtain a target chest X-ray image whose level of contrast in a neighboring area of a structure has been improved without being affected by pixels having pixel values whose frequencies are high.

Embodiments

Embodiments of the present disclosure will be described hereinafter with reference to the drawings. In the drawings, the same components are given the same reference numerals, and redundant description thereof is omitted as necessary.

First Embodiment

Figure 2:
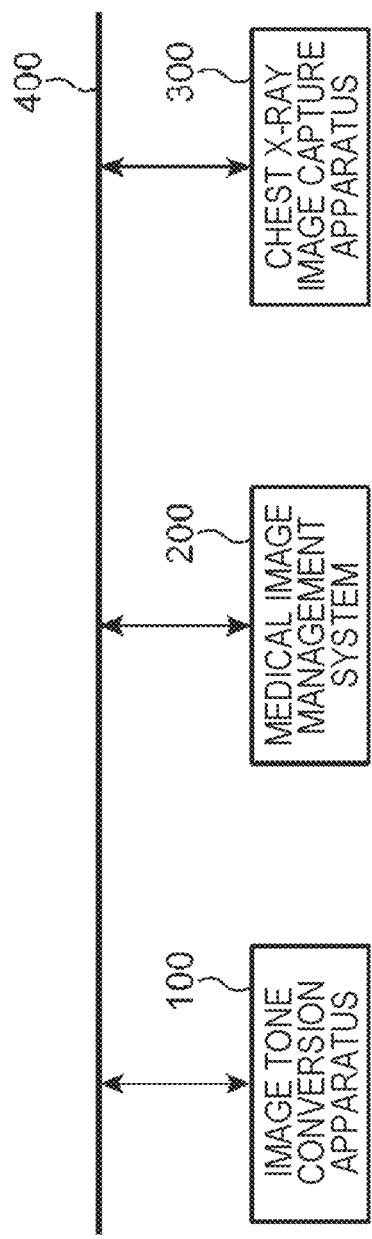
FIG. 2 is a block diagram illustrating a network configuration in a medical facility according to the first embodiment.

FIG. 1 is a block diagram schematically illustrating the configuration of an image tone conversion apparatus 100 that performs a method for converting tone of a chest X-ray image according to a first embodiment. FIG. 2 is a block diagram schematically illustrating a network configuration 410 in a medical facility.

As illustrated in FIG. 2, the network configuration 410 in the medical facility includes an intra network 400. The image tone conversion apparatus 100, a medical image management system 200, and a chest X-ray image capture apparatus 300 are connected to the intra network 400. The medical image management system 200 stores and manages chest X-ray images, computer tomography (CT) images, magnetic resonance imaging (MRI) images, and the like. The chest X-ray image obtaining apparatus 300 captures chest X-ray images of patients and persons who receive a medical examination. Chest X-ray images captured by the chest X-ray image capture apparatus 300 are transmitted and saved to the medical image management system 200.

The image tone conversion apparatus 100, the medical image management system 200, and the chest X-ray image capture apparatus 300 need not necessarily be connected to the intra network 400 in the same medical facility. The image tone conversion apparatus 100 and the medical image management system 200 may be software operating on a server in a data center outside the medical facility, a private cloud server, a public cloud server, or the like. The chest X-ray image capture apparatus 300 may be installed in a hospital or a vehicle that goes around to be used for a medical examination or the like. As the medical image management system 200, a picture archiving and communication system (PACS), for example, is used.

As illustrated in FIG. 1, the image tone conversion apparatus 100 includes a LUT storage unit 105, an image memory 106, a communication unit 107, a display 108, a central processing unit (CPU) 120, and a memory 121. The image tone conversion apparatus 100 is achieved, for example, by a personal computer.

The communication unit 107 communicates with the medical image management system 200 and the like over the intra network 400, The LUT storage unit 105 is achieved, for example, by a hard disk or a semiconductor memory. The LUT storage unit 105 stores a tone conversion LUT. The image memory 106 is achieved, for example, by a hard disk or a semiconductor memory. The image memory 106 stores obtained target chest X-ray images and chest X-ray images whose luminance has been converted. The display 108 has a function of displaying 8-bit (256-tone) images in the present embodiment. The display 108 is achieved by a liquid crystal display, for example, and displays a target chest X-ray image for a doctor or a radiologist, who is a user, to give an image diagnosis or perform image checking after the image is captured. The display 108 also displays chart information regarding a patient for whom the target chest X-ray image has been captured, a report input screen, on which a result of the image diagnosis is entered, and the like.

The memory 121 is achieved, for example, by a semiconductor memory. The memory 121 includes, for example, a read-only memory (ROM), a random-access memory (RAM), and an electrically erasable programmable read-only memory (EEPROM). The ROM of the memory 121 stores a control program for operating the CPU 120 according to the first embodiment.

The CPU 120 executes the control program according to the first embodiment stored in the memory 121 to function as a structure detection unit 111, a pixel extraction unit 112, a histogram calculation unit 113, a histogram equalization unit 114, a luminance conversion unit 115, a display control unit 116, and a communication control unit 117.

The structure detection unit 111 (an example of a detection unit) detects predefined structures from a target chest X-ray image saved in the image memory 106. The pixel extraction unit 112 (an example of an extraction unit) extracts pixel groups corresponding to neighboring areas of the structures detected by the structure detection unit 111. The histogram calculation unit 113 calculates luminance histograms from the pixel groups extracted by the pixel extraction unit 112. The histogram equalization unit 114 performs histogram equalization using the luminance histograms calculated by the histogram calculation unit 113. The histogram equalization unit 114 also reduces tone and obtains a tone conversion LUT. The histogram equalization unit 114 stores the tone conversion LUT in the LUT storage unit 105. The luminance conversion unit 115 converts luminance of all pixels of the target chest X-ray images using the tone conversion LUT stored in the LUT storage unit 105. The display control unit 116 displays the target chest X-ray image whose luminance has been converted by the luminance conversion unit 115 on the display 108. The communication control unit 117 (an example of an obtaining unit) controls the communication unit 107, Functions of the structure detection unit 111, the pixel extraction unit 112, the histogram calculation unit 113, the histogram equalization unit 114, the luminance conversion unit 115, and the display control unit 116 will be described later.

FIG. 3 is a flowchart schematically illustrating a process performed by the image tone conversion apparatus 100 according to the first embodiment. First, in step S50, the communication control unit 117 (an example of an obtaining unit) obtains a target chest X-ray image from the medical image management system 200 through the communication unit 107 and saves the obtained target chest X-ray image to the image memory 106. In step S100, the structure detection unit 111 reads the target chest X-ray image from the image memory 106 and detects one or more predefined structures from the target chest X-ray image.

Each of the one or more structures is (i) a line or an area in the chest X-ray image indicating an anatomical structure of a human body, (ii) a line or an area in the chest X-ray image indicating an area of an anatomical structure, or (iii) a boundary line in the chest X-ray image indicating a boundary between anatomical structures whose X-ray transmittances are different from each other.

Figure 5A:
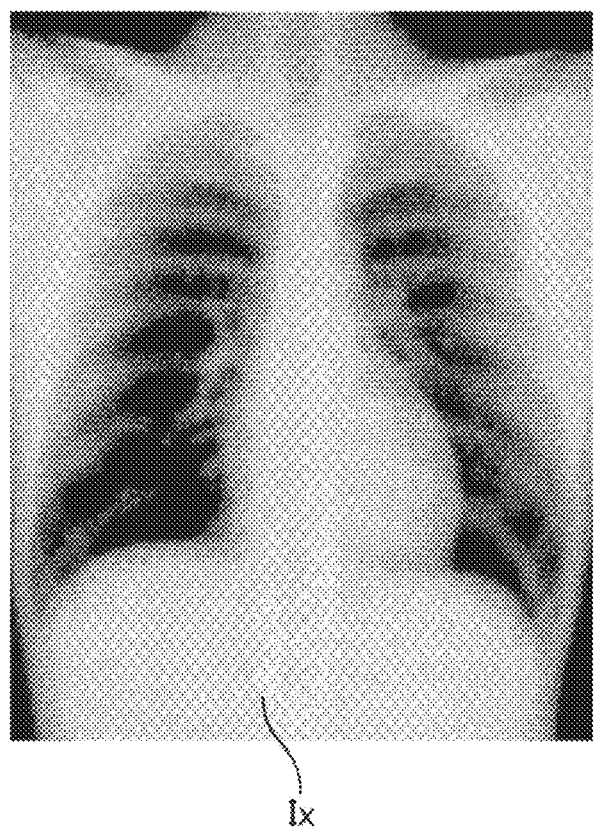
FIG. 5A is a diagram illustrating a chest X-ray image including a shadow in the right dorsal diaphragm.
Figure 5B:
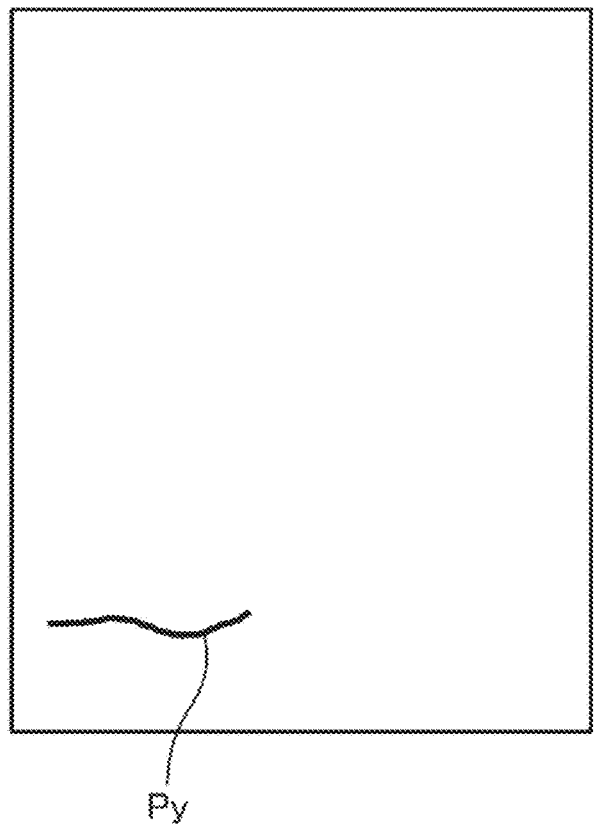
FIG. 5B is a diagram illustrating a mask image of a shadow in the right dorsal diaphragm.
Figure 5C:
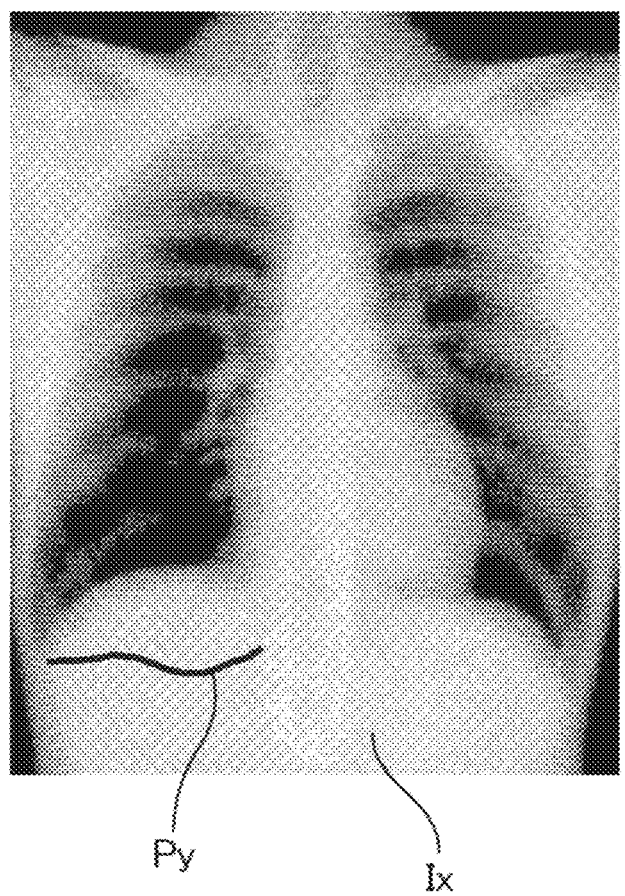
FIG. 5C is a diagram illustrating an image obtained by superimposing the mask image upon the chest X-ray image.
Figure 6A:
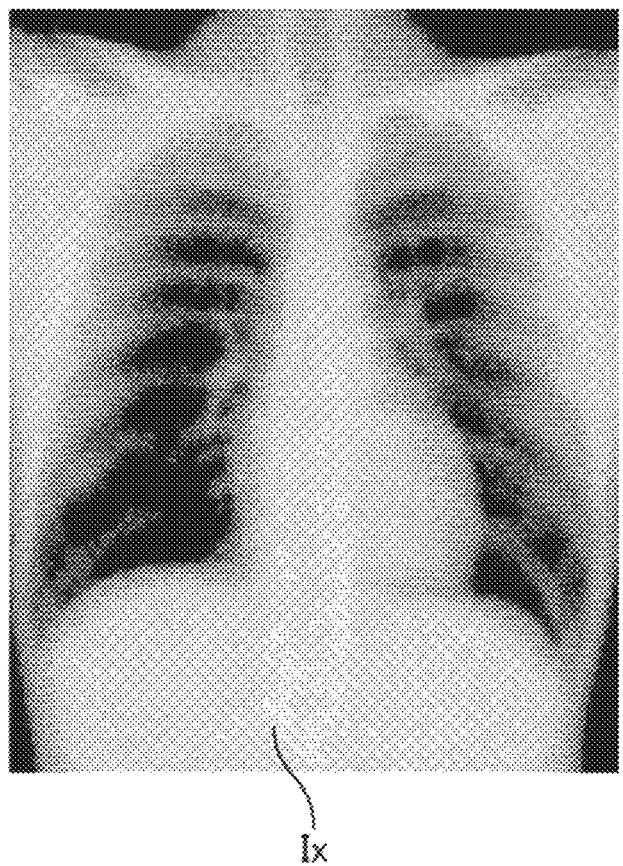
FIG. 6A is a diagram illustrating a chest X-ray image including the first thoracic vertebra.
Figure 6B:
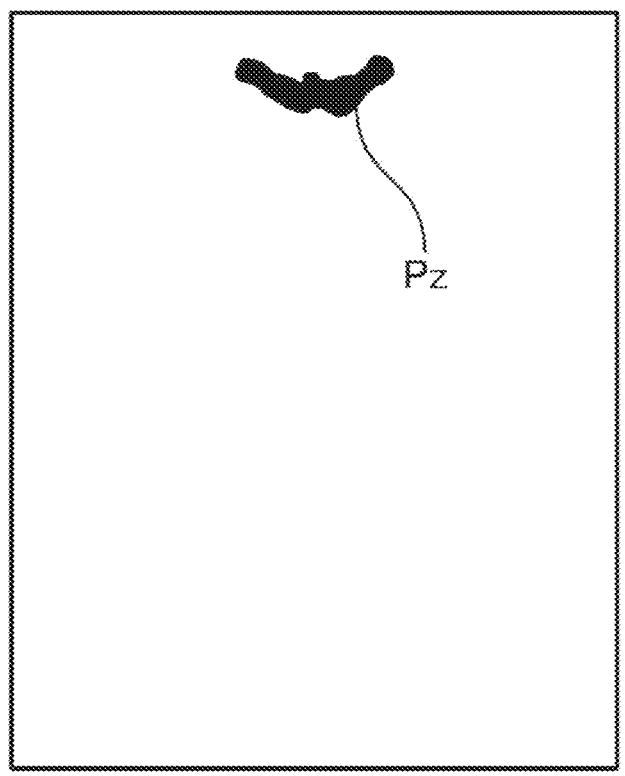
FIG. 6B is a diagram illustrating a mask image of the first thoracic vertebra.
Figure 6C:
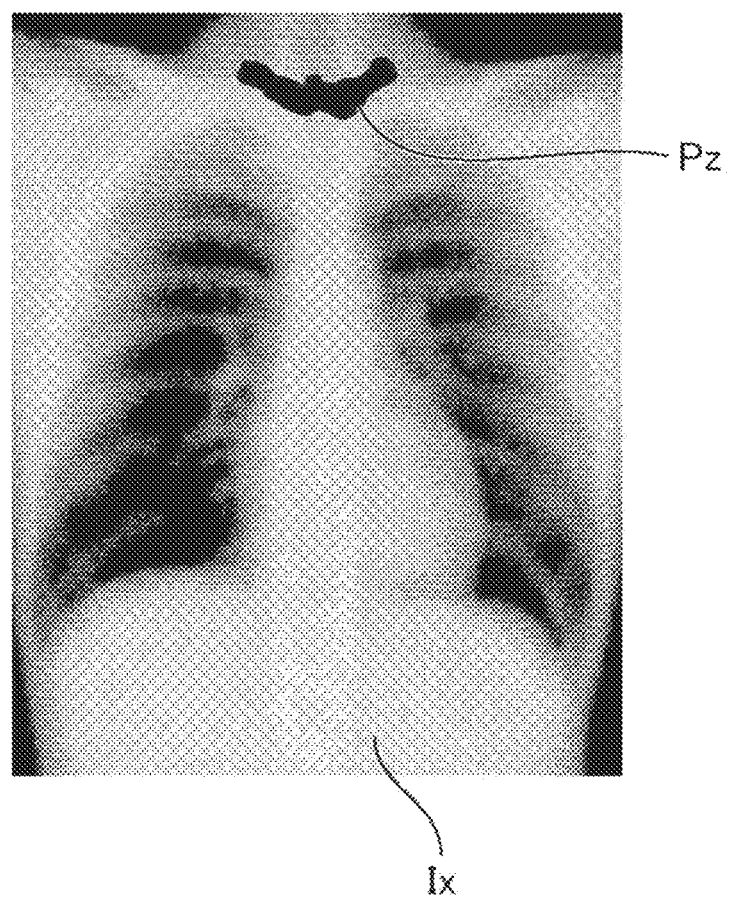
FIG. 6C is a diagram illustrating an image obtained by superimposing the mask image upon the chest X-ray image.

Each of the one or more structures is classified into a linear structure or an area structure. A linear structure may be a boundary line in a chest X-ray image, a line in a chest X-ray image indicating an anatomical structure, or a line in a chest X-ray image indicating a part of an anatomical structure. A structure that is not a linear structure, that is, a structure that is not regarded as a line, is defined as an area structure. Because there are linear structures wider than one pixel in images, however, linear structures and area structures can be indistinguishable from each other. For this reason, structures whose length divided by width is equal to or larger than a threshold, for example, may be defined as a linear structure. The threshold may be set at a value with which a structure can be regarded as a line and may be, say, 10, 100, or 1,000. FIGS. 4A to 4C and FIGS. 5A to 5C illustrate examples of the linear structure, and FIGS. 6A to 6C illustrate an example of the area structure.

Figure 4A:
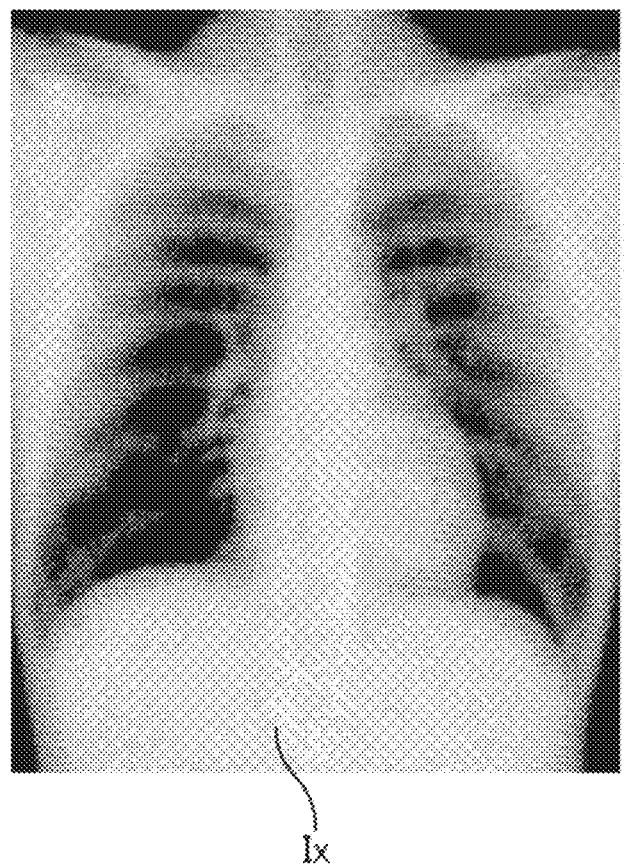
FIG. 4A is a diagram illustrating a chest X-ray image including a shadow in the descending aorta.
Figure 4B:
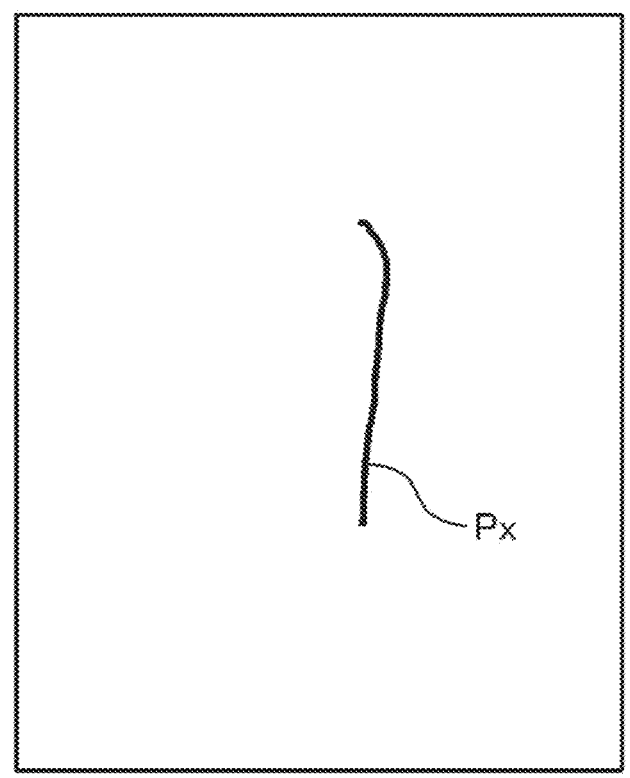
FIG. 4B is a diagram illustrating a mask image of the shadow in the descending aorta.
Figure 4C:
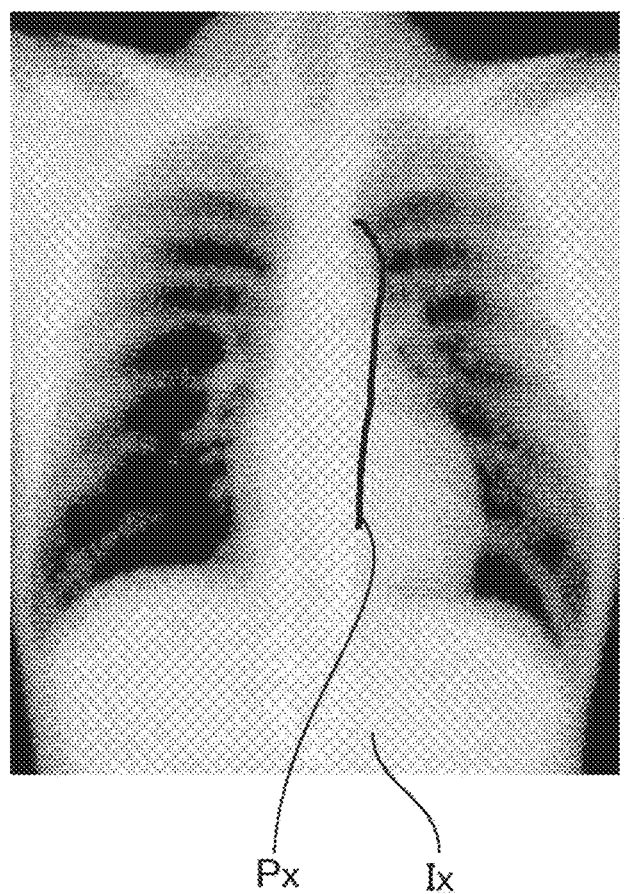
FIG. 4C is a diagram illustrating an image obtained by superimposing the mask image upon the chest X-ray image.

FIG. 4A is a diagram illustrating a chest X-ray image Ix including a shadow in the descending aorta (i.e., a boundary line caused by a difference in X-ray transmittance between the descending aorta and the lung parenchyma; an example of a first linear area). FIG. 4B is a diagram illustrating a mask image Px of the shadow in the descending aorta. FIG. 4C is a diagram illustrating an image displayed by superimposing the mask image Px illustrated in FIG. 4B upon the chest X-ray image Ix illustrated in FIG. 4A. FIG. 5A is a diagram illustrating the chest X-ray image Ix including a shadow in the right dorsal diaphragm (right dorsal lung base) (i.e., a boundary line caused by a difference in X-ray transmittance between a dorsal bottom of the lung parenchyma and ventral organs; an example of the first linear area). FIG. 5B is a diagram illustrating a mask image Py of the shadow in the right dorsal diaphragm. FIG. 5C is a diagram illustrating an image displayed by superimposing the mask image Py illustrated in FIG. 5B upon the chest X-ray image Ix illustrated in FIG. 5A, FIG. 6A is a diagram illustrating a chest X-ray image Ix including an area in which the first thoracic vertebra is projected. FIG. 6B is a diagram illustrating a mask image Pz of the first thoracic vertebra. FIG. 6C is a diagram illustrating an image displayed by superimposing the mask image Pz illustrated in FIG. 6B upon the chest X-ray image Ix illustrated in FIG. 6A.

A mask image expresses an area of a corresponding chest X-ray image occupied by a structure in binary representation or grayscale. In the present embodiment, a binary mask image is employed. A mask image is created and prepared by a person with a medical background as learning data used when the structure detection unit 111 is subjected to machine learning. The structure detection unit 111 subjected to machine learning outputs a mask image as a result of processing of a target chest X-ray image.

In the present embodiment, an artificial neural network is used as means for performing machine learning on the structure detection unit 111. More specifically, U-Net disclosed in O. Ronneberger, P. Fischer, and T. Brox, "U-Net: Convolutional Networks for Biomedical Image Segmentation", Medical Image Computing and Computer-Assisted Intervention (MICCAI), Springer, LNCS, Vol. 9351: 234-241, 2015 is used as an artificial neural network that performs semantic segmentation for extracting a target area from a target image in units of pixels. "Semantic segmentation" refers to recognition of an image in units of pixels.

Figure 7:
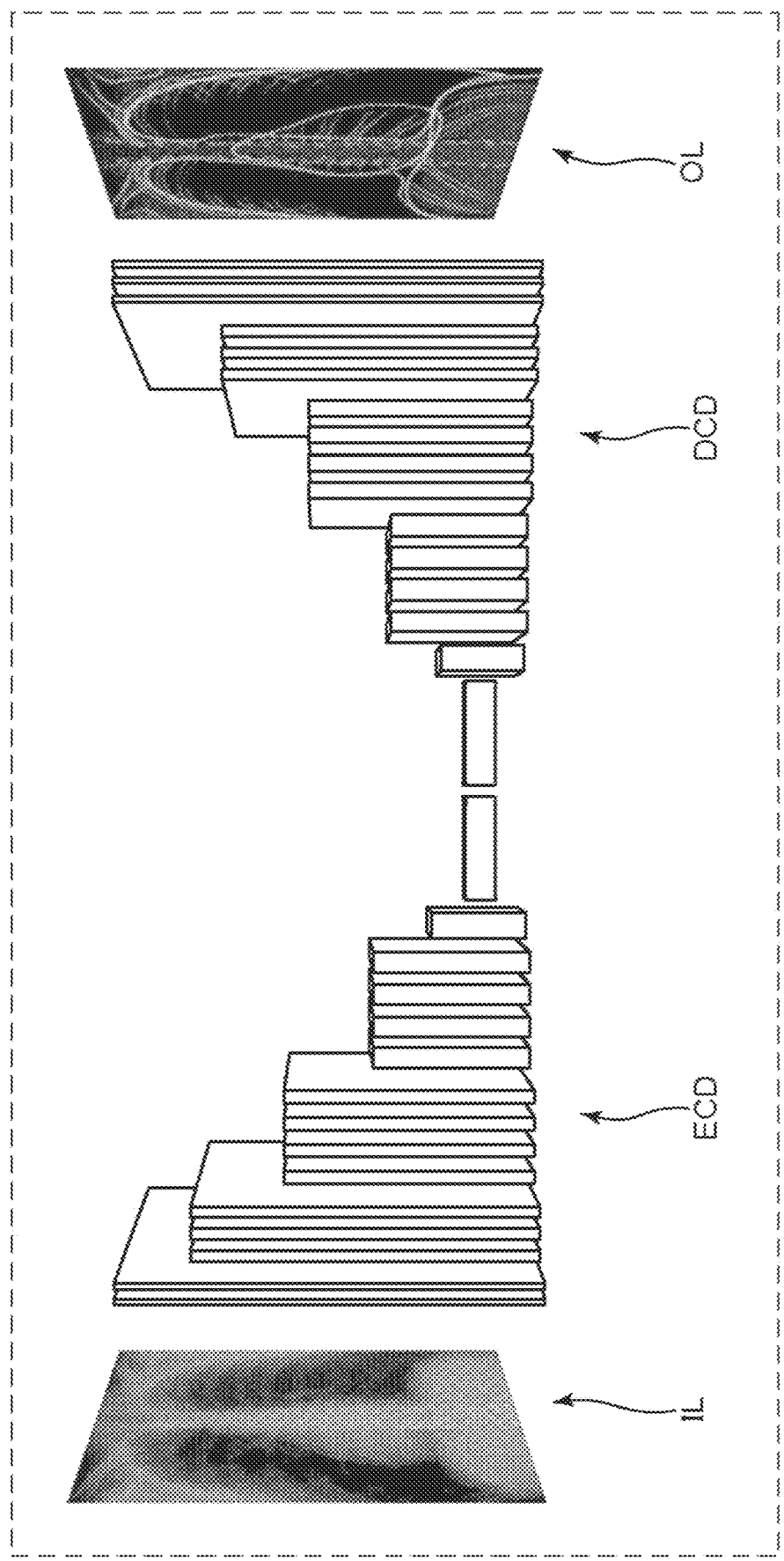
FIG. 7 is a diagram schematically illustrating the architecture of U-Net.

FIG. 7 is a diagram schematically illustrating the architecture of U-Net. U-Net is a convolutional neural network including an encoder ECD and a decoder DCD illustrated in FIG. 7. An input image is input to an input layer IL of U-Net, and U-Net outputs an output image to an output layer OL. Machine learning is performed by giving U-Net a large number of pairs of an input image, such as those illustrated in FIGS. 4A, 5A, and 6A, and a mask image, such as those illustrated in FIGS. 4B, 5B, and 6B.

More specifically, a large number of chest X-ray images Ix, such as that illustrated in FIG. 4A, are input to U-Net, and machine learning is performed such that U-Net outputs mask images Px, such as that illustrated in FIG. 4B. As a result, a structure detection unit 111 for detecting a shadow in the descending aorta is generated. In addition, a large number of chest X-ray images Ix, such as that illustrated in FIG. 5A, are input to U-Net, and machine learning is performed such that U-Net outputs mask images Py, such as that illustrated in FIG. 5B. As a result, a structure detection unit 111 for detecting a shadow in the right dorsal diaphragm is generated. In addition, a large number of chest X-ray images Ix, such as that illustrated in FIG. 6A, are input to U-Net, and machine learning is performed such that U-Net outputs mask images Pz, such as that illustrated in FIG. 6B. As a result, a structure detection unit 111 for detecting the first thoracic vertebra is generated. When a target chest X-ray image is input to the structure detection unit 111 for detecting a shadow in the descending aorta after the machine learning, for example, a shadow in the descending aorta is detected as an area of a structure defined in the machine learning.

In the present embodiment, machine learning is performed on U-Nets that detect a total of N predefined structures (N is an integer equal to or larger than 1) to prepare N U-Nets subjected to the machine learning. These N U-Nets subjected to the machine learning are used as the structure detection unit 111. Alternatively, another neural network, such as one disclosed in L. Long, E. Shelhamer, and T. Darrell, "Fully Convolutional Networks for Semantic Segmentation", CVPR, 2015, may be used instead of U-Net as an artificial neural network that performs semantic segmentation.

In step S200 illustrated in FIG. 3, the pixel extraction unit 112 detects structures 0, . . . , k, . . . , and N−1. The pixel extraction unit 112 then extracts a group $P_0$ of pixel values of pixels included in a neighboring area $R_0$ of structure 0, . . . , a group $P_k$ of pixel values of pixels included in a neighboring area $R_k$ of structure k, . . . , and a group $P_{N-1}$ of pixel values of pixels included in a neighboring area $R_{N-1}$ of structure N−1. The group $P_k$ of pixels is represented by expression (1). Expression (16) indicates that the group $P_k$ of pixel values is a group of pixel values $p_{x,y}$ at coordinates (x, y) included in the neighboring area $R_k$.

$$P_k = \{p_{x,y} | p_{x,y} \in R_k\} \quad (1)$$

Figure 8A:
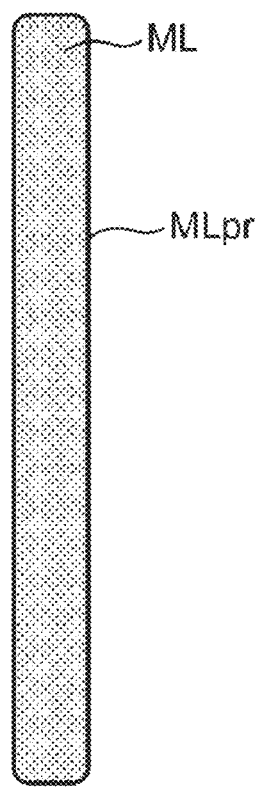
FIG. 8A is a diagram schematically illustrating an example of a linear structure.
Figure 8B:
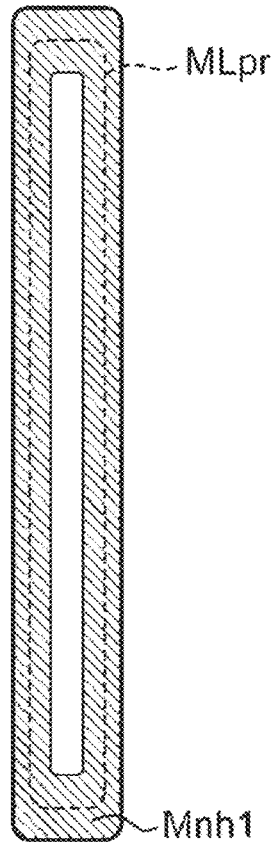
FIG. 8B is a diagram schematically illustrating an example of a neighboring area of the linear structure illustrated in FIG. 8A.

FIG. 8A is a diagram schematically illustrating an example of a linear structure. FIG. 8B is a diagram schematically illustrating an example of a neighboring area of the linear structure illustrated in FIG. 8A. FIG. 9A is a diagram schematically illustrating an example of an area structure. FIG. 9B is a diagram schematically illustrating an example of a neighboring area of the area structure illustrated in FIG. 9A.

In FIGS. 8A and 8B, the pixel extraction unit 112 extracts a contour MLpr of a linear structure ML, which is a structure detected by the structure detection unit 111. The pixel extraction unit 112 calculates a neighboring area Mnh1 by expanding the contour MLpr outward and inward by a certain number of pixels through a morphological process. The pixel extraction unit 112 extracts a group of pixels values of pixels included in the neighboring area Mnh1.

Figure 19:
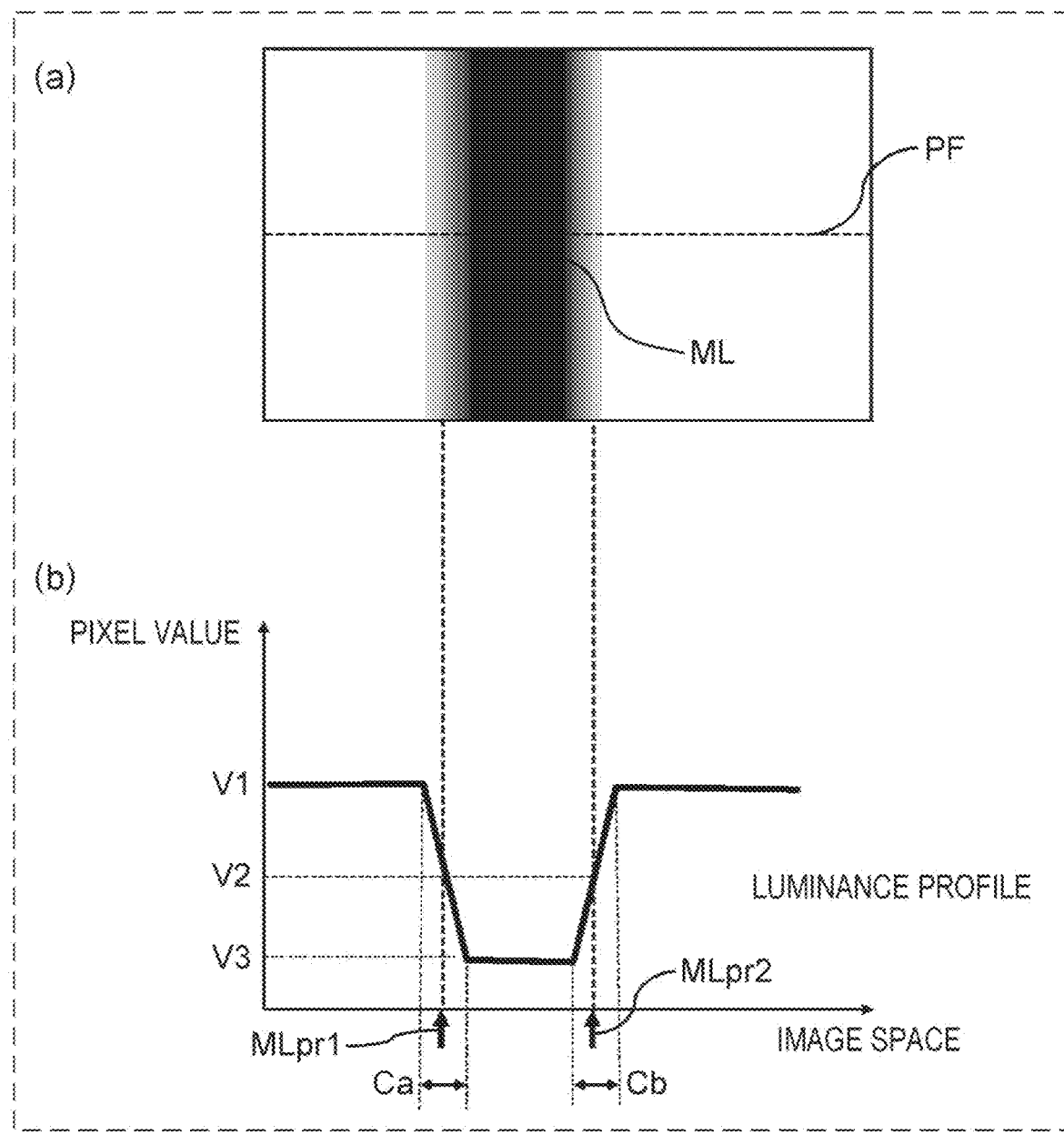
FIG. 19 is a diagram illustrating a reason for expanding a contour by a certain number of pixels.

Here, a reason for expanding the contour MLpr by the certain number of pixels will be described with reference to FIG. 19. FIG. 19(a) is an enlarged view of the linear structure ML, and FIG. 19(b) illustrates a luminance profile on a line (denoted by PF in FIG. 19(a)) across the linear structure ML. A horizontal axis in FIG. 19(b) represents an image space (x coordinate) of FIG. 19(a), and a vertical axis represents luminance on the linear PF in an image illustrated in FIG. 19(a). In many images, adjacent pixel values smoothly change when enlarged as illustrated in FIG. 19(b) even at edges. Boundary lines of the linear structure ML illustrated in FIG. 19(a), therefore, are recognized as MLpr1 and MLpr2 indicated in FIG. 19(b). Since the present disclosure aims to improve a level of contrast of the linear structure ML, pixel values (luminance values) V1 and V3 illustrated in FIG. 19(b) need to be used in subsequent histogram equalization. If pixels within ranges (denoted by Ca and Cb in FIG. 19(b)) only slightly away from the boundary lines MLpr1 and MLpr2 illustrated in FIG. 19(b) are used, however, the level of contrast of the linear structure ML is not sufficiently improved. Pixels having the pixel values V1 and V3 are therefore used by expanding the contour MLpr1 and MLpr2 by the certain number of pixels. The certain number of pixels may be determined, for example, by sequentially calculating differences between adjacent pixels (i.e., changes in luminance) near the contour MLpr in a direction that goes away from the contour MLpr until the changes in luminance become a certain percentage (e.g., 5% to 10%) of changes in the luminance of the linear structure ML (|V1-V3| in FIG. 19(b)).

In FIGS. 9A and 9B, the pixel extraction unit 112 extracts a contour RGpr of an area structure RG, which is a structure detected by the structure detection unit 111. The pixel extraction unit 112 calculates a neighboring area Rnh1 by expanding the contour RGpr outward and inward by a certain number of pixels through a morphological process. The pixel extraction unit 112 extracts a group of pixel values of pixels included in the neighboring area Rnh1. As described with reference to FIGS. 8A to 9B, in the present embodiment, the neighboring area $R_k$ is obtained by expanding the contour RGpr of the structure RG inward and outward by the certain number of pixels.

In step S300 illustrated in FIG. 3, the pixel extraction unit 112 creates a union S of the group $P_0$ of pixel values, the group $P_k$ of pixel values, ..., and the group $P_{N-1}$ of pixel values represented by expression (2).

$$S = P_0 \cup P_1 \cup P_2 \cup P_3 \cup \ldots \cup P_{N-1} \qquad (2)$$

Next, in step S400, the histogram calculation unit 113 creates a histogram of the pixel values included in the union S created in step S300. The created histogram is called a "luminance histogram". The pixel values indicate luminance values.

In step S500, the histogram equalization unit 114 generates a contrast conversion expression for histogram equalization using the created luminance histogram. A luminance value q(z) after contrast conversion is represented by expression (3), which is the contrast conversion expression, using a luminance value z included in a target chest X-ray image before the contrast conversion, a frequency H(z) of the luminance value z included in the union S, the number A of elements of the union S (i.e., the number of pixels included in the union S defined by expression (2)), and a luminance maximum value Zmax. That the frequency H(z) is a frequency of a pixel value, that is, the luminance value z, included in the union S means that the frequency H(z) does not include the frequency of the luminance value z outside the neighboring areas $R_0$ to $R_{N-1}$ in the target chest X-ray image.

In the present embodiment, for example, tone of a target chest X-ray image before tone reduction is 12 bits (4,096 tones), and tone of the target chest X-ray image after the tone reduction is 8 bits (256 tones). Here, the above-described contrast conversion is performed before the tone reduction, and the luminance maximum value Zmax is 4,095.

$$q(z) = \frac{Z_{max}}{A} \cdot \sum_{i=0}^{z} H(i) \qquad (3)$$

The luminance value q(z) after the histogram equalization in expression (3) is calculated for the luminance value z equal to or larger than 0 but equal to or smaller than Z. When z=0, for example,
q(0)=H(0)Zmax/A
When z=1, for example,
q(1)={H(0)+H(1)}Zmax/A
When z=2, for example,
q(2)={H(0)+H(1)+H(2)}Zmax/A
When z=Zmax=4,095, for example,
q(4095)={H(0)+H(4095)}Zmax/A In step S600, the histogram equalization unit 114 calculates an 8-bit luminance value t(z) from the 12-bit luminance value q(z) using expression (4), which is a tone reduction expression, to convert a 12-bit image into an 8-bit image.

$$t(z) = q(z)/16 \qquad (4)$$

In expressions (3) and (4), decimals are rounded off or dropped to obtain the integral luminance values q(z) and t(z). In expression (4), therefore, the luminance value q(z) is an integer within a range of 0 to 4,095, and the luminance value t(z) is an integer within a range of 0 to 255.

The histogram equalization unit 114 also creates a tone conversion LUT 1000 (FIG. 10). The histogram equalization unit 114 stores the created tone conversion LUT 1000 in the LUT storage unit 105.

FIG. 10 is a diagram schematically illustrating an example of the tone conversion LUT 1000. As illustrated in FIG. 10, the original luminance value z and the luminance value t(z) after the histogram equalization and the tone reduction are associated in the tone conversion LUT 1000 with each other. As described above, the luminance value z is an integer within the range of 0 to 4,095, and the luminance value t(z) is an integer within the range of 0 to 255.

The neighboring areas Mnh1 and Rnh1 of the structures illustrated in FIGS. 8B and 9B, respectively, include both pixels constituting the structures and pixels that do not constitute the structures. That is, the union S includes, for each of the N structures, pixels constituting the structure and pixels that do not constitute the structure. As a result, by performing histogram equalization on the luminance histogram of the union S, the tone conversion LUT 1000 for improving a level of contrast between each of the N structures and corresponding boundaries in the target chest X-ray image.

In step S700 illustrated in FIG. 3, the luminance conversion unit 115 converts the luminance of all pixels of the chest X-ray image using the tone conversion LUT 1000 created in step S600. In step S800, the display control unit 116 displays, on the display 108, the target chest X-ray image converted into the 8-bit image as a result of the tone conversion. Luminance conversion for improving levels of contrast of all the N structures and tone conversion for reducing tone of all the N structures are thus performed. The target chest X-ray image converted into the 8-bit image as a result of the tone conversion is thus displayed on the display 108.

Definitions of terms will be described hereinafter. "Tone conversion" refers to luminance conversion including both (A) contrast conversion for improving a level of contrast of an image and (B) tone reduction for converting (reducing) the number of tones for expressing gradation in an image. Histogram equalization and gamma correction are a specific example of a method used in (A) contrast conversion. "Luminance conversion", on the other hand, does not refer to a specific conversion process but simply refers to conversion of luminance (pixel values). "Tone" herein refers to "gradation in an image" in a broad sense and "the number of shades in a digital image" (e.g., 256 tones) in a narrow sense. A pixel value may indicate a luminance value.

Although the neighboring area $R_k$ is obtained by expanding the contour RGpr of the structure RG inward and outward by the certain number of pixels in step S200 in the present embodiment, the neighboring area $R_k$ is not limited to this.

Figure 11A:
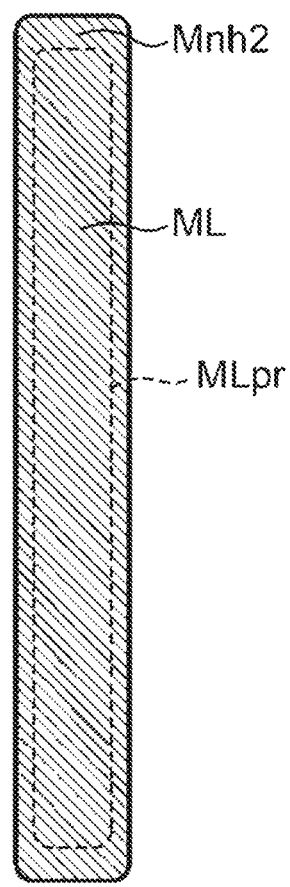
FIG. 11A is a diagram schematically illustrating another example of the neighboring area of the linear structure illustrated in FIG. 8A.
Figure 11B:
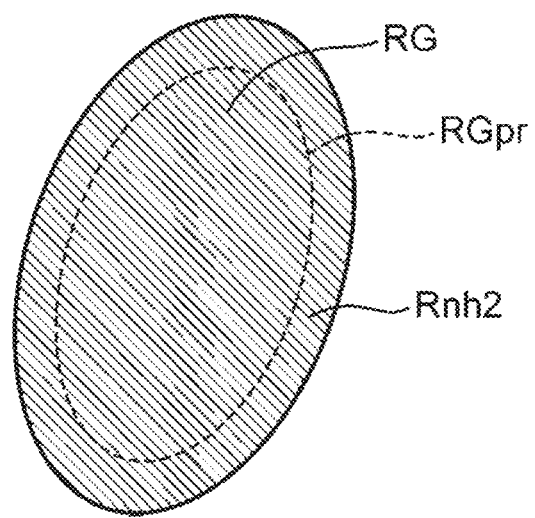
FIG. 11B is a diagram schematically illustrating another example of the neighboring area of the area structure illustrated in FIG. 9A.

FIG. 11A is a diagram schematically illustrating another example of the neighboring area of the linear structure illustrated in FIG. 8A. FIG. 11B is a diagram schematically illustrating another example of the neighboring area of the area structure illustrated in FIG. 9A.

In the examples illustrated in FIGS. 11A and 11B, the pixel extraction unit 112 determines areas obtained by expanding the linear structure ML and the area structure RG outward by a certain number of pixels as neighboring areas Mnh2 and Rnh2, respectively. The neighboring areas Mnh2 and Rnh2 of the structures ML and RG illustrated in FIGS. 11A and 11B include both pixels constituting the structures and pixels outside the structures. The number of pixels constituting the structures, however, is larger than in the case of the neighboring areas Mnh1 and Rnh1 illustrated in FIGS. 8B and 9B. A tone conversion LUT for improving a level of contrast within a structure and a level of contrast between the structure and corresponding boundaries can therefore be obtained for all the N structures by performing histogram equalization on a luminance histogram of a union S of pixels included in the neighboring areas Mnh2 and Rnh2 illustrated in FIGS. 11A and 11B. When a structure is a bone such as a rib or a collarbone, for example, a level of contrast of trabecula improves.

As described above, according to the first embodiment of the present disclosure, a structure including a linear structure formed of a first linear area drawn by projecting anatomical structures whose X-ray transmittances are different from each other or a second linear area drawn by projecting an anatomical structure including a wall of a trachea, a wall of a bronchus, or a hair line is detected. A tone conversion LUT is obtained by generating a contrast conversion expression for histogram equalization using a histogram of a group of pixels values of pixels corresponding to a neighboring area of the detected structure and a tone reduction expression for reducing tone. Luminance of the entirety of a target chest X-ray image is converted using the tone conversion LUT. As a result, tone conversion for improving a level of contrast of a structure important in making a diagnosis can be performed without being affected by pixels having luminance values whose frequencies are high.

Second Embodiment

Figure 12:
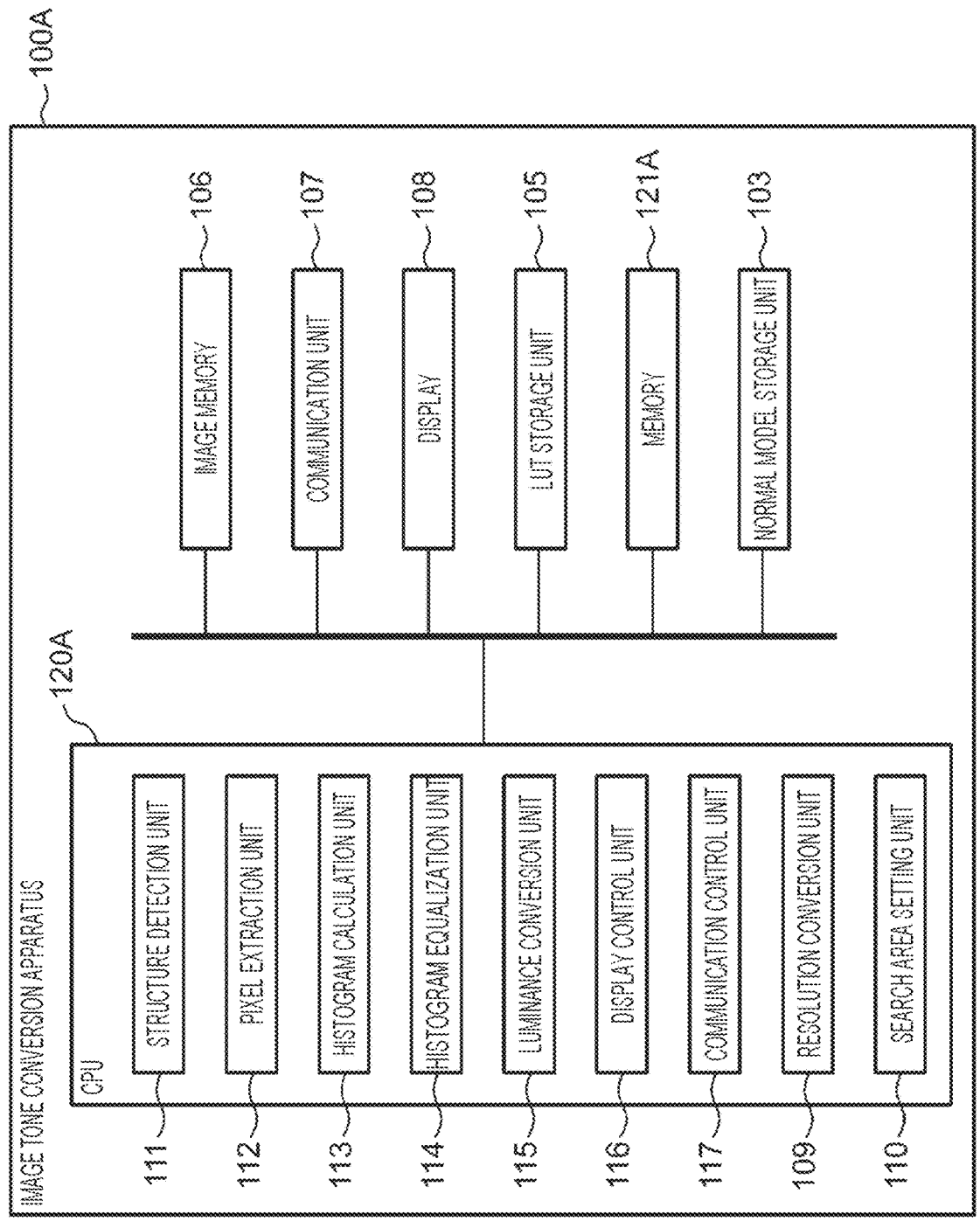
FIG. 12 is a block diagram illustrating the configuration of an image tone conversion apparatus according to a second embodiment.

FIG. 12 is a block diagram schematically illustrating the configuration of an image tone conversion apparatus 100A that performs a method for converting tone of a chest X-ray image according to a second embodiment. Unlike the image tone conversion apparatus 100 illustrated in FIG. 1, the image tone conversion apparatus 100A illustrated in FIG. 12 newly includes a normal model storage unit 103 and also includes a CPU 120A instead of the CPU 120 and a memory 121A instead of the memory 121.

The normal model storage unit 103 (an example of a position memory) stores information regarding relative positional relationships between structures in advance. The memory 121A is configured in the same manner as the memory 121, and includes, for example, a ROM, a RAM, and an EEPROM. The ROM of the memory 121A stores a control program for operating the CPU 120A according to the second embodiment.

The CPU 120A executes the control program according to the second embodiment stored in the memory 121A to function as the structure detection unit 111, the pixel extraction unit 112, the histogram calculation unit 113, the histogram equalization unit 114, the luminance conversion unit 115, the display control unit 116, a resolution conversion unit 109, and a search area setting unit 110.

The resolution conversion unit 109 creates images having different resolutions by performing reduction conversion of more than one stages on a target chest X-ray image. The resolution conversion unit 109 stores the created images in the image memory 106. The search area setting unit 110 sets an area to be searched for a structure in an image of a higher resolution using a result of detection of a structure performed by the structure detection unit 111 on a low-resolution image and the information regarding relative positional relationships between structures stored in the normal model storage unit 103.

Next, a process performed by the image tone conversion apparatus 100A according to the second embodiment will be described. The overall process is the same as in the first embodiment described with reference to the flowchart of FIG. 3.

Figure 13:
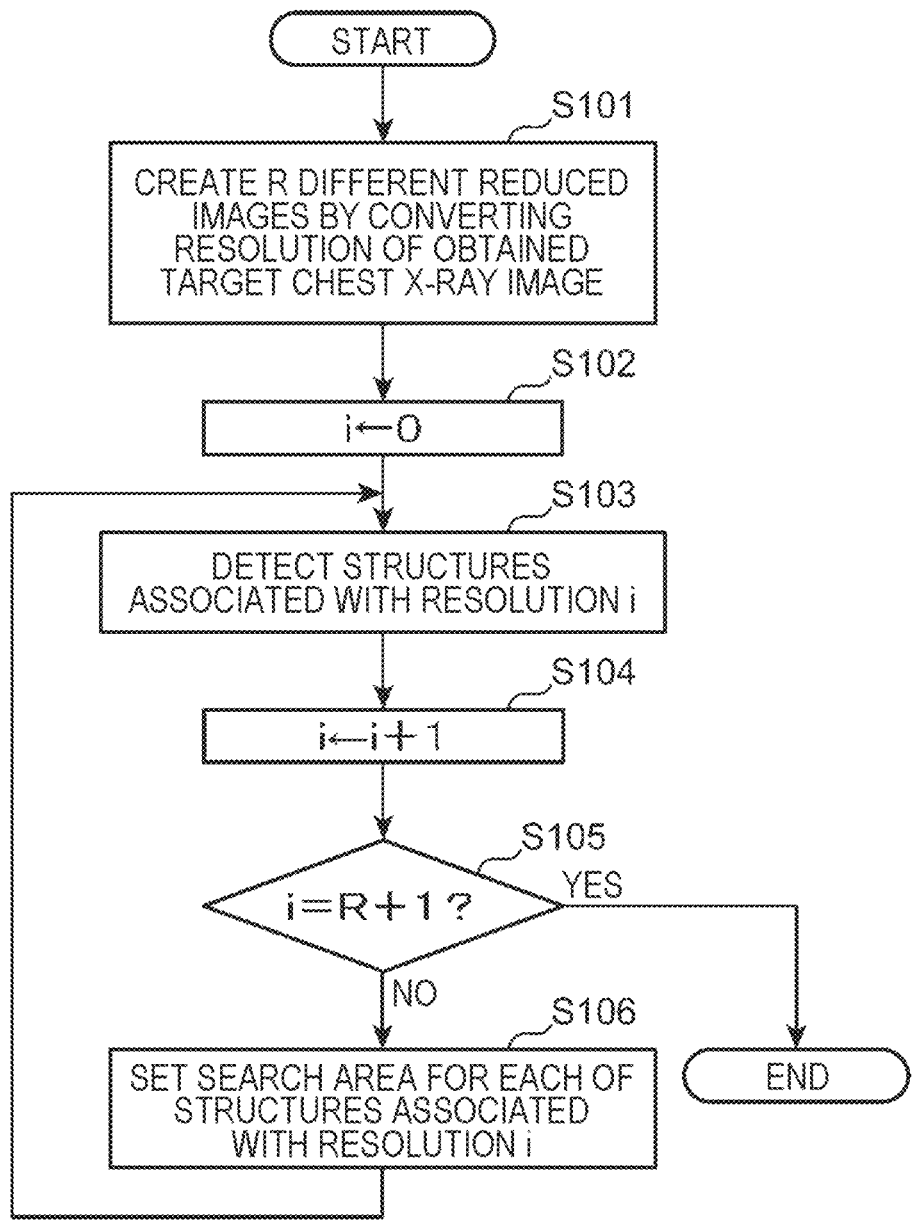
FIG. 13 is a flowchart illustrating a process for detecting structures according to the second embodiment.

FIG. 13 is a flowchart schematically illustrating a process performed by the image tone conversion apparatus 100A according to the second embodiment in step S100 (FIG. 3). FIG. 14 is a diagram schematically illustrating resolution information 2600.

In step S141 illustrated in FIG. 13, the resolution conversion unit 109 creates R (e.g., R=3 in the present embodiment) different reduced images for the target chest X-ray image obtained in step S50 (FIG. 3). The resolution of a chest X-ray image is usually 2,000 to 3,000 pixels each side. In the second embodiment, the resolution of the target chest X-ray image is, for example, 2,048×2,048. Resolutions of three different reduced images created by the resolution conversion unit 109 are, for example, 1,024×1,024, 512× 512, and 256×256.

In the second embodiment, resolution i is set at 0, 1, 2, and 3 for the images in ascending order of resolution. That is, the resolution i of the 256×256 image is 0, the resolution i of the 512×512 image is 1, the resolution i of the 1,024×1,024 image is 2, and the resolution i of the 2,048×2,048 image (i.e., the original image) is 3. The resolution conversion unit 109 stores the created low-resolution reduced images in the image memory 106.

Next, in step S102, the structure detection unit 111 reads the image whose resolution i=0 (i.e., the lowest-resolution, namely, 256×256, image) from the image memory 106 as a structure detection target image. Next, in step S103, the structure detection unit 111 detects structures associated with the image of the resolution i (the image whose resolution i=0 in a first round of step S103) on the basis of the resolution information 2600 (FIG. 14).

As illustrated in FIG. 14, the resolution information 2600 includes a structure identifier (ID) field 2601 and a resolution i field 2602. In the structure ID field 2601, N structures whose structure IDs are 0 to N−1 and that are defined in the first embodiment are set. In the resolution i field 2602, the resolution of an image to be used to detect a corresponding structure in the structure ID field 2601 is defined. A structure whose structure ID is 0, for example, is detected from the image whose resolution i is 0, that is, the 256×256 image. Although only one resolution is set for each structure in FIG. 14, the number of resolutions is not limited to this. For example, two or more resolution may be set depending on a structure, and the structure may be detected using images of the two or more resolutions.

As in the first embodiment, the structure detection unit 111 detects a structure using U-Net disclosed in "U-Net: Convolutional Networks for Biomedical Image Segmentation", As described above, U-net is a type of convolutional neural network. A convolutional neural network is a type of deep neural network. A neural network including two or more intermediate layers is called a deep neural network. During machine learning for a deep neural network and detection of a structure, processing speed is usually increased using a graphics processing unit (GPU). At this time, it might be difficult to handle a high-resolution image due to a restriction to the memory capacity of the GPU. In such a case, an image obtained by reducing an original image and decreasing the resolution of the original image is input to U-Net. In this case, however, detection performance for small structures, such as linear structures, can decrease. For this reason, in the second embodiment, the structure detection unit 111 detects a relatively large (an example of a first size) structure from a low-resolution image and a relatively small (an example of a second size) structure within a limited search area by trimming a high-resolution image.

In step S104 illustrated in FIG. 13, the structure detection unit 111 increments the resolution i. In a first round of step S104, i=1, In step S105, the structure detection unit 111 determines whether the resolution i has exceeded an upper limit (i.e., i=R+1) of resolution. If the resolution i has exceeded the upper limit of resolution (YES in step S105), the process illustrated in FIG. 13 ends, and step S100 (FIG. 3) ends. If the resolution i has not exceeded the upper limit of resolution (NO in step 3105), the process proceeds to step S106.

Figure 15:
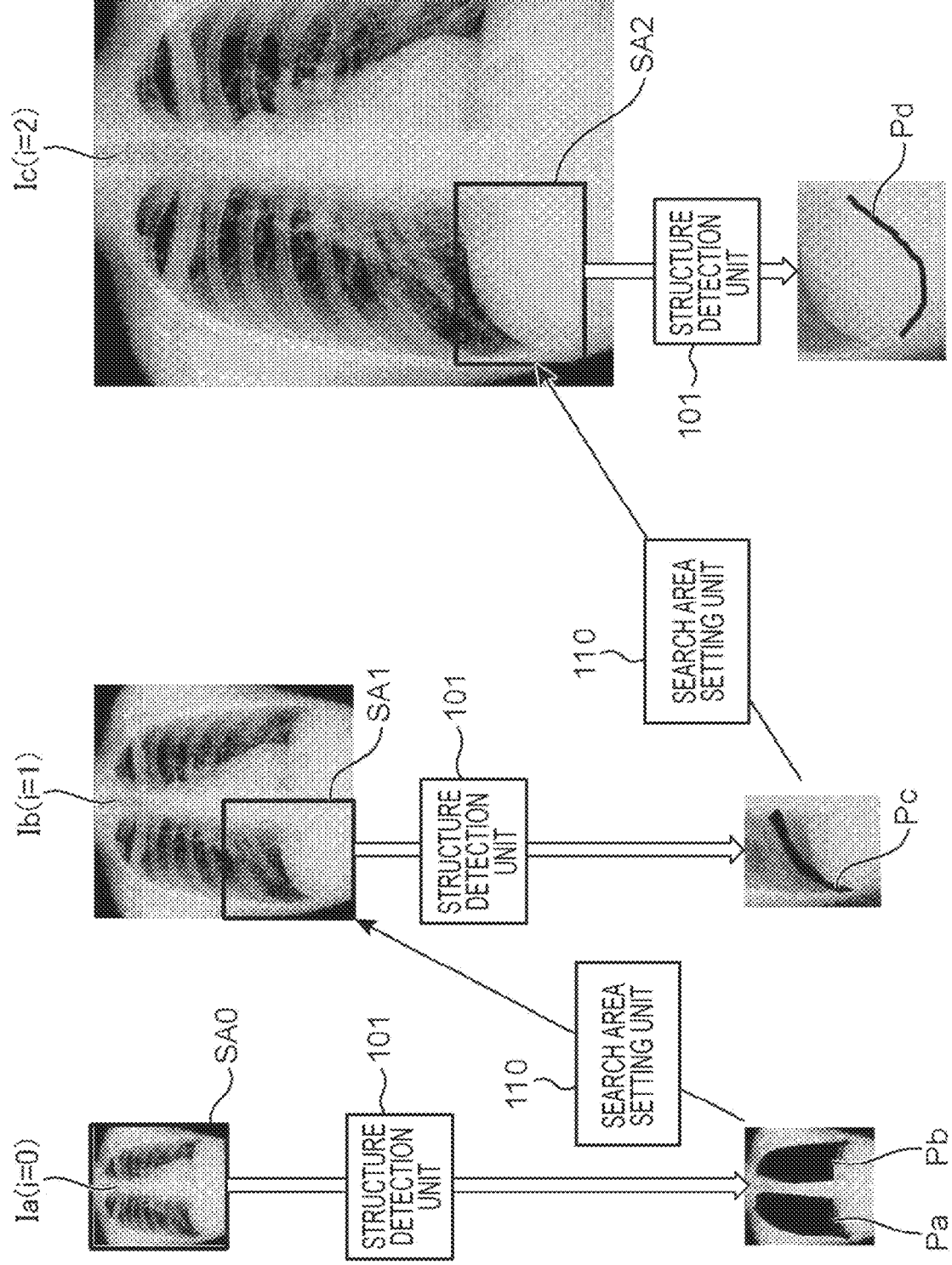
FIG. 15 is a diagram schematically illustrating steps illustrated in FIG. 13.

In step S106, the search area setting unit 110 selects all structures associated with the resolution i (i=1 in a first round of step S106) on the basis of the resolution information 2600 illustrated in FIG. 14 and sets a search area for an image of the resolution i for each of the corresponding structures. Relative positional relationships between structures are obtained from a large number of binary mask images of structures, such as those illustrated in FIGS. 4B, 5B, and 6B and saved to the normal model storage unit 103 in advance. The search area setting unit 110 reads the relative positional relationships saved in the normal model storage unit 103 and uses the relative positional relationships to set search areas. After step S106 ends, the process returns to step 3103, In a second round of step S103, the structure detection unit 111 detects structures associated with the image of the resolution i (the image whose resolution i=1 in the second step S103) on the basis of the resolution information 2600 (FIG. 14). Steps S103 to S106 are then repeated while the resolution i does not exceed the upper limit of resolution (NO in step S105), FIG. 15 is a diagram schematically illustrating steps S103 to S106 illustrated in FIG. 13, In FIG. 15, first, the structure detection unit 111 detects structures Pa and Pb from a chest X-ray image la whose resolution is low (i=0) (step 3103). In the example illustrated in FIG. 15, the structure Pa is the right lung field, and the structure Pb is the left lung field. In the present embodiment, the chest X-ray image la is an example of a first X-ray image, the resolution i=0 (256×256) is an example of a first resolution, and the size of the structures Pa and Pb is an example of the first size.

Next, the resolution i is incremented (step S104), and the search area setting unit 110 sets a search area in a chest X-ray image Ib whose resolution is intermediate (i=1) (step S106). Although FIG. 15 illustrates only a search area SA1, a search area is set in step S106 for each of the structure IDs associated with the resolution i. Each search area is set using a structure to be detected indicated by a structure ID and a positional relationship between already detected structures (the structures Pa and Pb in the example illustrated in FIG. 15) saved in the normal model storage unit 103.

Next, the structure detection unit 111 detects a structure in the search area of the chest X-ray image Ib of the intermediate resolution (i=1) (step S103). Although FIG. 15 illustrates only a structure Pc detected in the search area SA1, a structure to be detected is detected in step S163 in each search area. In the present embodiment, the chest X-ray image Ib is an example of a second X-ray image, the resolution i=1 (512×512) is an example of a second resolution, and the size of the structure Pc is an example of the second size.

Next, the resolution i is incremented (step S104), and the search area setting unit 110 sets a search area in a chest X-ray image Ic whose resolution is high (i=2) (step S106). Although FIG. 15 illustrates only a search area SA2, a search area is set in step S106 for each of the structure IDs associated with the resolution i. Each search area is set using a structure to be detected indicated by a structure ID and a positional relationship between already detected structures (the structures Pa and Pb in the example illustrated in FIG. 15) saved in the normal model storage unit 103.

Next, the structure detection unit 111 detects a structure in the search area of the chest X-ray image Ic of the high resolution (i=2) (step S103). Although FIG. 15 illustrates only a structure Pd detected in the search area SA2, a structure to be detected is detected in step S103 in each search area.

As described above, according to the second embodiment of the present disclosure, when a deep neural network such as U-Net is used as the structure detection unit 111, a decrease in structure detection performance can be suppressed since a search area smaller than a target chest X-ray image is set when a high-resolution image is used even if the memory capacity of the GPU is low.

Furthermore, tone conversion for improving a level of contrast of a structure important in making a diagnosis can be performed without being affected by pixels having luminance values whose frequencies are high, which is the effect produced by the first embodiment.

Third Embodiment

Figure 16:
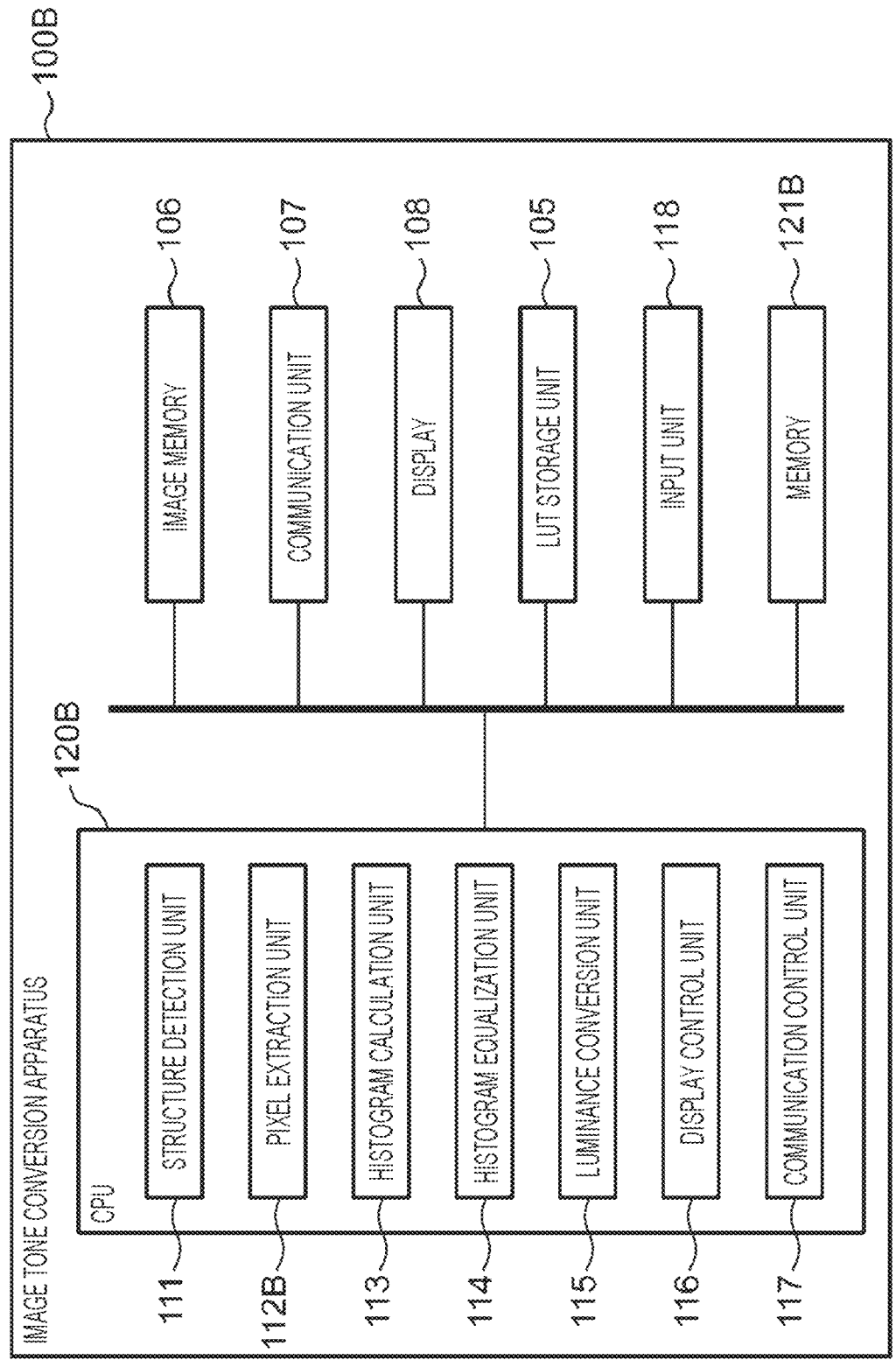
FIG. 16 is a block diagram illustrating the configuration of an image tone conversion apparatus according to a third embodiment.

FIG. 16 is a block diagram schematically illustrating the configuration of a tone conversion apparatus 144E that performs a method for converting tone of a chest X-ray image according to a third embodiment. Unlike the image tone conversion apparatus 100 illustrated in FIG. 1, the tone conversion apparatus 1468 illustrated in FIG. 16 newly includes an input unit 118 and also includes a CPU 120B instead of the CPU 120 and a memory 121B instead of the memory 121.

The input unit 118 is operated by a user such as a doctor or a radiologist. The memory 121B is configured in the same manner as the memory 121 and includes, for example, a ROM, a RAM, and an EEPROM. The ROM of the memory 121B stores a control program for operating the CPU 120B according to the third embodiment.

The CPU 120B executes the control program according to the third embodiment stored in the memory 121B to function as the structure detection unit 111, a pixel extraction unit 112B, the histogram calculation unit 113, the histogram equalization unit 114, the luminance conversion unit 115, the display control unit 116, and the communication control unit 117.

The pixel extraction unit 112 according to the first embodiment extracts pixel values of pixels corresponding to neighboring areas of all the N structures detected by the structure detection unit 111. The pixel extraction unit 112E according to the third embodiment, on the other hand, pixel values of pixels corresponding to neighboring areas of structures selected by the user using the input unit 118 among the N structures detected by the structure detection unit 111.

Figure 17:
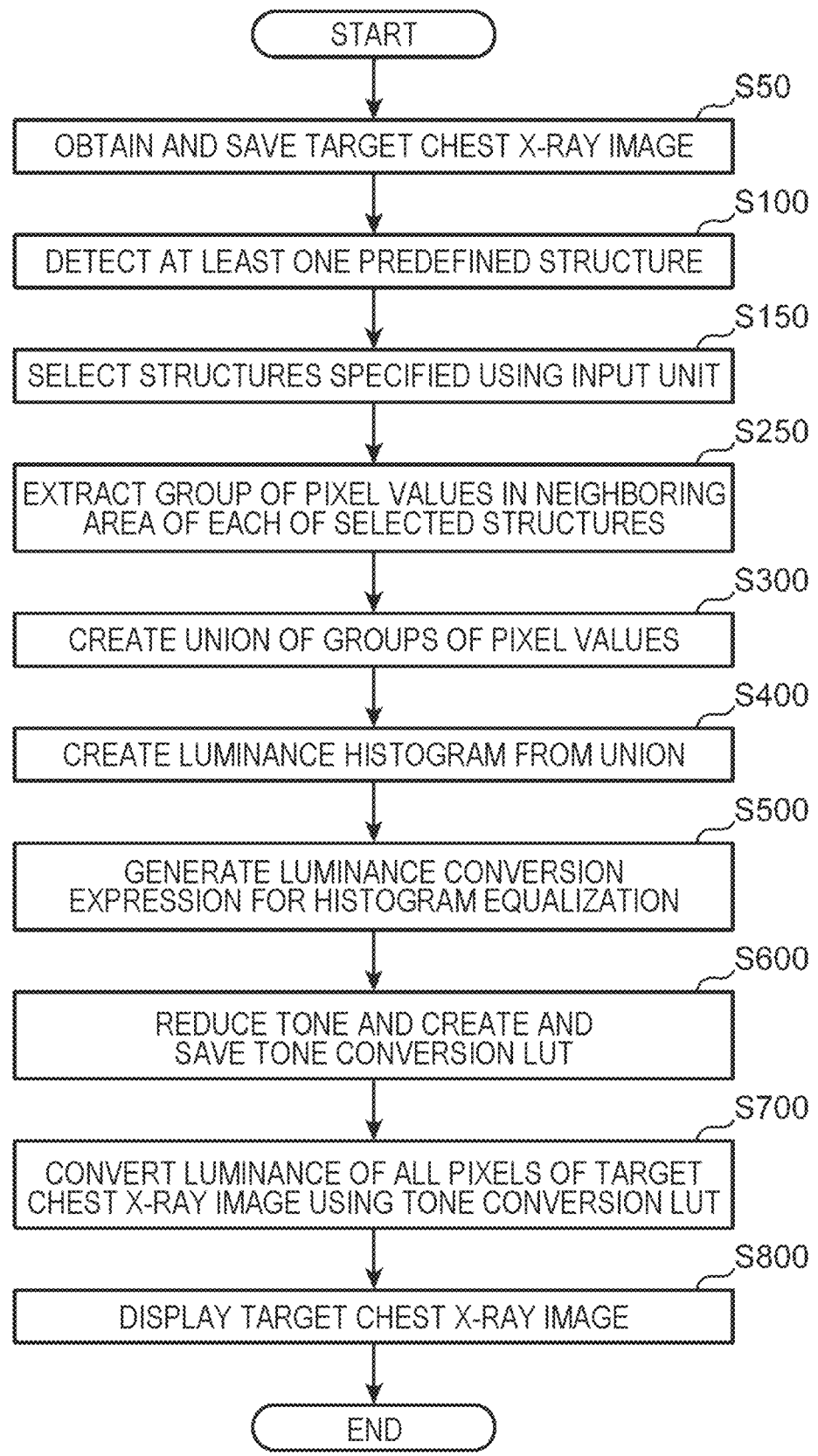
FIG. 17 is a flowchart according to the third embodiment.

FIG. 17 is a flowchart schematically illustrating a process performed by the tone conversion apparatus 100B according to the third embodiment. Steps S50 and S100 illustrated in FIG. 17 are the same as those illustrated in FIG. 3. In step S150, which follows step S100, the pixel extraction unit 112B selects structures specified using the input unit 118 among the N structures detected by the structure detection unit 111. In step S250, the pixel extraction unit 112B extracts a group of pixel values corresponding to a neighboring area of each of the selected structures, Steps S300 to S800 illustrated in FIG. 17 are the same as those illustrated in FIG. 3.

According to the third embodiment, tone conversion for improving levels of contrast of structures desired by the user can be performed.

Fourth Embodiment

Figure 18:
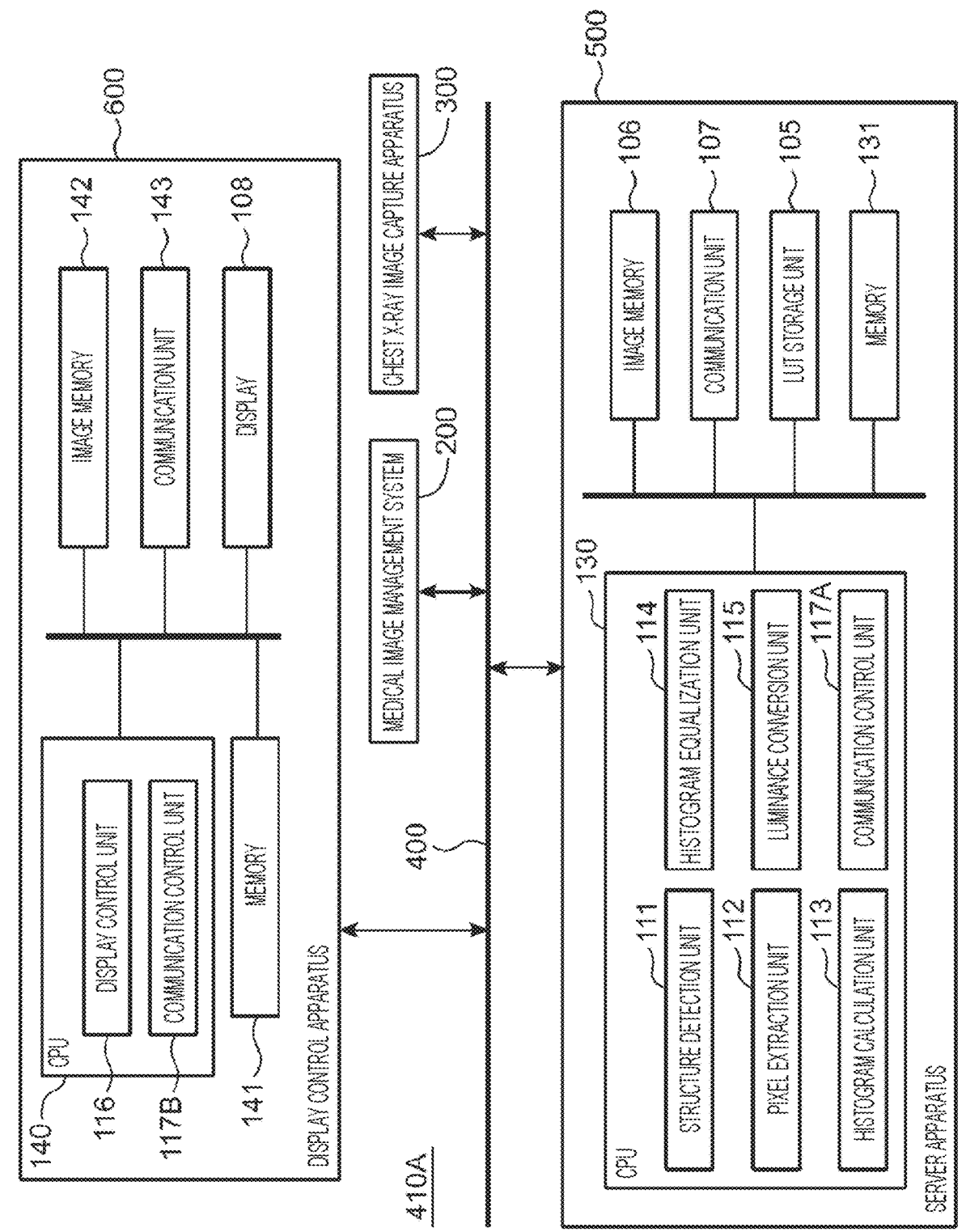
FIG. 18 is a block diagram illustrating a network configuration in a medical facility according to a fourth embodiment.

FIG. 18 is a block diagram schematically illustrating a network configuration 410A in a medical facility according to a fourth embodiment. As illustrated in FIG. 18, a server apparatus 500, a display control apparatus 600, the medical image management system 200, and the chest X-ray image capture apparatus 300 are connected to an intra network 400 in the medical facility in the fourth embodiment.

The server apparatus 500, the display control apparatus 600, the medical image management system 200, and the chest X-ray image capture apparatus 300 need not necessarily be connected to the intra network 400 in a single medical facility. The display control apparatus 600 and the medical image management system 200 may be software that operates on a server in a data center outside the medical facility, a private cloud server, a public cloud server, or the like, instead.

As illustrated in FIG. 18, the server apparatus 500 includes the LUT storage unit 105, the image memory 106, the communication unit 107, a CPU 130, and a memory 131. The memory 131 is achieved, for example, by a semiconductor memory. The memory 131 includes, for example, a ROM, a RAM, and an EEPROM. The ROM of the memory 131 stores a control program for operating the CPU 130.

The CPU 130 executes the control program stored in the memory 131 to function as the structure detection unit 111, the pixel extraction unit 112, the histogram calculation unit 113, the histogram equalization unit 114, the luminance conversion unit 115, and a communication control unit 117A. The communication control unit 117A obtains a target chest X-ray image whose luminance has been converted by the luminance conversion unit 115 to the display control apparatus 600 through the communication unit 107.

The display control apparatus 600 (an example of a terminal apparatus) is achieved, for example, by a tablet computer and carried by a medical worker such as a doctor or a radiologist. As illustrated in FIG. 18, the display control apparatus 600 includes a CPU 140, a memory 141, an image memory 142, a communication unit 143, and the display 108.

The memory 141 is achieved, for example, by a semiconductor memory. The memory 141 includes, for example, a ROM, a RAM, and an EEPROM. The ROM of the memory 141 stores a control program for operating the CPU 140. The CPU 140 executes the control program stored in the memory 141 to function as the display control unit 116 and a communication control unit 117B.

The communication control unit 1178 receives, through the communication unit 143, data regarding a target chest X-ray image whose luminance has been converted and that has been transmitted from the server apparatus 500 and stores the received data in the image memory 142. The display control unit 116 displays, on the display 108, the target chest X-ray image whose luminance has been converted and that is stored in the image memory 142.

According to the fourth embodiment, the same effect as that produced by the first embodiment can be produced. Alternatively, the CPU 130 of the server apparatus 500 may function as the structure detection unit 111, the pixel extraction unit 112, the histogram calculation unit 113, the histogram equalization unit 114, the luminance conversion unit 115, the communication control unit 117, the resolution conversion unit 109 (FIG. 12), and the search area setting unit 110 (FIG. 12). In this case, the same effect as that produced by the second embodiment can be produced.

The present disclosure can be used in diagnosis aiding systems for chest X-ray images to be interpreted and interpretation education systems for medical students or interns.

What is claimed is:

1. A method for converting tone of a chest X-ray image, the method being performed by a computer of an image tone conversion apparatus that converts tone of a target chest X-ray image, which is a chest X-ray image to be interpreted, the method comprising:
   obtaining the target chest X-ray image;
   detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;
   extracting a pixel group corresponding to a neighboring area of the structure;
   generating a contrast conversion expression for histogram equalization using a histogram of the pixel group; and
   converting luminance of each pixel value in entirety of the target chest X-ray image using the contrast conversion expression.

2. The method according to claim 1,
   wherein the model obtained as a result of the machine learning is a model subjected to the machine learning such that the structure is detected in a learning chest X-ray image, which is a chest X-ray image in a normal state, using a neural network that performs prediction in units of pixels.

3. The method according to claim 2,
   wherein, in the detecting, a first X-ray image is created by converting a resolution of the target chest X-ray image into a first resolution, which is lower than the resolution of the target chest X-ray image,
   wherein a second X-ray image is created by converting the resolution of the target chest X-ray image into a second resolution, which is higher than the first resolution but equal to or lower than the resolution of the target chest X-ray image,
   wherein a structure of a first size is detected from the first X-ray image,
   wherein a search area smaller than the second X-ray image is set in the second X-ray image on a basis of a result of the detection of the structure of the first size, and
   wherein a structure of a second size, which is smaller than the first size, is detected in the search area.

4. The method according to claim 3,
   wherein, in the detection of the structure of the first size, an anatomical structure is detected from the first X-ray image as the structure of the first size, and
   wherein, in the detection of the structure of the second size, a linear structure is detected in the search area of the second X-ray image as the structure of the second size.

5. The method according to claim 3,
   wherein, in the setting of the search area, the search area is set using a relative positional relationship between the structure of the first size and the structure of the second size read from a position memory storing the relative positional relationship in advance.

6. The method according to claim 1,
   wherein, in the extracting, an area obtained by expanding a contour of the structure outward and inward by a certain number of pixels is determined as the neighboring area of the structure.

7. The method according to claim 1,
   wherein, in the extracting, an area obtained by expanding the structure outward by a certain number of pixels is determined as the neighboring area of the structure.

8. The method according to claim 1,
   wherein, in the extracting, all detected structures are used.

9. The method according to claim 1, further comprising:
   selecting, by a user, at least one of detected structures,
   wherein, in the extracting, only the at least one of the detected structures selected by the user is used.

10. The method according to claim 1, further comprising:
    displaying, on a display, the target chest X-ray image whose luminance has been converted,
    wherein, in the converting of the luminance, the luminance of each pixel value in the entirety of the target chest X-ray image is converted using the contrast conversion expression and a tone reduction expression for reducing the tone of the target chest X-ray image.

11. A storage medium storing a program for causing a computer of an image tone conversion apparatus that converts tone of a target chest X-ray image, which is a chest X-ray image to be interpreted, to perform a process, the storage medium being nonvolatile and computer-readable, the process comprising:
    obtaining the target chest X-ray image;
    detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;
    extracting a pixel group corresponding to a neighboring area of the structure;
    generating a contrast conversion expression for histogram equalization using a histogram of the pixel group; and
    converting luminance of each pixel value in entirety of the target chest X-ray image using the contrast conversion expression.

12. An image tone conversion apparatus comprising:
    an obtainer that obtains a target chest X-ray image, which is a chest X-ray image to be interpreted;
    a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;
    an extractor that extracts a pixel group corresponding to a neighboring area of the structure;
    an equalizer that generates a contrast conversion expression for histogram equalization using a histogram of the pixel group; and
    a luminance converter that converts luminance of each pixel value in entirety of the target chest X-ray image using the contrast conversion expression.

13. A server apparatus comprising:
    an obtainer that obtains a target chest X-ray image, which is a chest X-ray image to be interpreted;
    a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;

an extractor that extracts a pixel group corresponding to a neighboring area of the structure; and an equalizer that generates a contrast conversion expression for histogram equalization using a histogram of the pixel group; and a luminance converter that converts luminance of each pixel value in entirety of the target chest X-ray image using the contrast conversion expression; and a communication controller that transmits the target chest X-ray image whose luminance has been converted to an external terminal apparatus.

14. A conversion method comprising:

obtaining an X-ray image;

detecting a linear area in the X-ray image;

determining a neighboring area of the linear area;

providing a conversion expression, first pixel values of first pixels being included in the linear area or the neighboring area of the linear area; and converting the first pixel values and second pixel values of second pixels into resulting values using the conversion expression, the second pixels including (i) pixels that are included in the X-ray image but that are not included in the linear area and (ii) pixels that are included in the X-ray image but that are not included in the neighboring area;

wherein the conversion expression is $$q(z) = \frac{Z_{max}}{A} \cdot \sum_{i=0}^{z} H(i) \tag{3}$$

where z is a pixel value included in the X-ray image, where q(z) is a resulting value of the pixel value z included in the resulting values, where H(i) is a number of pixels whose pixel values are i among the first pixel values, where Zmax is a maximum pixel value of each of the pixels of the X-ray image, and where A is a number of first pixels.

* * * * *

UNITED STATES PATENT AND TRADEMARK OFFICE
CERTIFICATE OF CORRECTION

PATENT NO. : 11,406,340 B2
APPLICATION NO. : 17/088657
DATED : August 9, 2022
INVENTOR(S) : Kenji Kondo It is certified that error appears in the above-identified patent and that said Letters Patent is hereby corrected as shown below:

On the Title Page

In Item (73) Assignee: change "Panasonic Corporation, Osaka (JP)" to --Panasonic Holdings Corporation, Osaka (JP)--

Signed and Sealed this
Fourteenth Day of November, 2023

Katherine Kelly Vidal
*Director of the United States Patent and Trademark Office*